US012766012B2

(12) United States Patent
Elcock et al.

(10) Patent No.: US 12,766,012 B2
(45) Date of Patent: Oct. 20, 2026

(54) EXPANDABLE TIBIAL TRAY INSERT TRIAL

(71) Applicant: GLOBUS MEDICAL, INC., Audubon, PA (US)

(72) Inventors: Aaron Elcock, Philadelphia, PA (US); Jason Zappacosta, Philadelphia, PA (US); Andrew Mike, Phoenixville, PA (US); Ryan Frasca, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 407 days.

(21) Appl. No.: 18/423,434

(22) Filed: Jan. 26, 2024

(65) Prior Publication Data

US 2024/0261115 A1 Aug. 8, 2024

Related U.S. Application Data

(60) Provisional application No. 63/517,382, filed on Aug. 3, 2023, provisional application No. 63/482,889, filed on Feb. 2, 2023.

(51) Int. Cl.
*A61F 2/46* (2006.01)
*A61F 2/38* (2006.01)

(52) U.S. Cl.
CPC .............. *A61F 2/4684* (2013.01); *A61F 2/38* (2013.01); *A61F 2/4657* (2013.01); *A61F 2002/4658* (2013.01)

(58) Field of Classification Search
CPC ........ A61F 2/4684; A61F 2/38; A61F 2/4657; A61F 2002/4658; A61F 2/389
See application file for complete search history.

(56) References Cited

U.S. PATENT DOCUMENTS

| | | | | |
|---|---|---|---|---|
| 9,277,965 | B2 * | 3/2016 | Dietz | A61F 2/4657 |
| 2009/0216332 | A1 | 8/2009 | Splieth et al. | |
| 2015/0018957 | A1 | 1/2015 | Nichols et al. | |
| 2019/0110905 | A1 * | 4/2019 | Cabot | A61B 17/025 |
| 2022/0280309 | A1 | 9/2022 | Yoon et al. | |
| 2024/0238102 | A1 * | 7/2024 | Nonnenmann | A61B 17/025 |

FOREIGN PATENT DOCUMENTS

| | | | | |
|---|---|---|---|---|
| JP | H11513274 A | 11/1999 | | |
| JP | 2013013729 A | 1/2013 | | |
| JP | 2015532863 A | 11/2015 | | |
| JP | 6521671 B2 * | 8/2025 | | A61F 2/38 |

* cited by examiner

*Primary Examiner* — Bruce E Snow

(57) ABSTRACT

Knee arthroplasty trials, systems, and methods regarding the same. The knee arthroplasty trial system may include an expandable tibial tray trial having top and bottom plates, an actuation screw retained in the bottom plate, and an expansion ramp configured to slide along the bottom plate and lift the top plate as the ramp translates forward. The actuation screw may define a helical cut with step portions, and the expansion ramp includes a pin configured to engage the helical cut of the actuation screw. When the actuation screw is rotated, the pin rides along the helical cut and is configured to rest within one of the step portions, thereby ensuring that the expandable tibial tray trial expands only to discrete thicknesses.

20 Claims, 21 Drawing Sheets

EXPANDABLE TIBIAL TRAY INSERT TRIAL

CROSS-REFERENCE TO RELATED APPLICATIONS

This application claims priority to U.S. Provisional Application No. 63/482,889, filed Feb. 2, 2023, and U.S. Provisional Application No. 63/517,382, filed Aug. 3, 2023, which are incorporated by reference herein in their entireties for all purposes.

FIELD OF THE INVENTION

The present application relates generally to knee arthroplasty, and more particularly, to knee arthroplasty trials for evaluating the fit of permanent implants and methods regarding the same.

BACKGROUND OF THE INVENTION

Knee arthroplasty, often called a knee replacement, is a surgical procedure used to reconstruct and resurface a knee that has been damaged, for example, by arthritis. Total knee arthroplasty (TKA) devices may replace both the tibiofemoral joint and the patellofemoral joint. The tibiofemoral joint is where the tibia and the femur articulate. The patellofemoral joint is where the patella and the femur articulate. To replace the tibiofemoral joint, the knee arthroplasty may include a femoral implant secured to the distal end of the femur (or thigh bone), a tibial tray implant secured to the proximal end of the tibia (or shin bone), and an insert disposed therebetween. The femoral and tibial implants cap the ends of the femur and tibia, respectively, which form the knee joint, thereby reconstructing the knee. To replace the patellofemoral joint, the knee arthroplasty may include a patella prostheses to replace the backside of the patella and form a replacement articulating surface which interfaces with the femoral implant.

In order to properly determine the implant sizes, one or more trials may be used by the surgeon during the surgical procedure. Trials are temporary components which match the geometry of the final implants with corresponding sizes so that surgeons can evaluate the fit of a given size before permanently implanting the final components. The sizing of each of these components is needed to match the native anatomy as closely as possible. The femoral and tibial trial components may vary in size with respect to the anterior posterior (AP) and medio-lateral (ML) directions, and the inserts may also be available in a number of various thicknesses. This requires many trials to cover all of the tibial/femoral sizes and insert thicknesses. The trialing process may be time intensive and may require multiple trials to find the proper fit. Discrete fixed-height trials can be difficult to insert and remove from the joint space, since an optimal fit may be quite snug. This can become time-consuming and frustrating if a surgeon needs to try several thicknesses before feeling confident that the correct thickness has been chosen. Shim systems may include a set of shims which can be inserted to increase the height of the stack, but these also require a number of components, are time consuming, and can be complicated to assemble. Thus, there exists a need for improved trialing devices, which decrease the overall count of instruments and improve efficiency during the trial reduction process.

SUMMARY OF THE INVENTION

To meet this and other needs, knee arthroplasty trials, systems, and methods are provided. In particular, the knee arthroplasty trials may include an expandable tibial trial with a screw-driven ramp mechanism to create separation between top and bottom plates. The screw may include stepped increments, which allow the trial to be set at distinct heights corresponding to available tibial insert sizes. The expandable tibial trial may include an articular insert, for example, which slides or snaps onto the expandable trial. The complete knee arthroplasty trial system may include the expandable tibial trial with attached articular insert and a femoral trial configured to mate with the articular insert, thereby mimicking the proper function of the knee.

According to one embodiment, a knee arthroplasty trial system includes an expandable tibial tray trial having top and bottom plates, an actuation screw retained in the bottom plate, and an expansion ramp configured to slide along the bottom plate and lift the top plate as the ramp translates forward. The actuation screw defines a helical cut with step portions, and the expansion ramp includes a pin configured to engage the helical cut of the actuation. When the actuation screw is rotated, the pin rides along the helical cut and is configured to rest within one of the step portions, thereby ensuring that the expandable tibial tray trial expands only to discrete thicknesses.

The knee arthroplasty trial system may include one or more of the following features. The expansion ramp may include a ramped body with a pair of vertical support walls defining a channel therebetween for receiving the actuation screw. The pin may be a cross-pin extending between the pair of vertical support walls and across the channel. The ramped body may define an upper inclined plane providing a sloped surface configured to mate with a corresponding surface on the top plate. The ramped body may include a pair of rails extending from a bottom surface of the ramped body, and the rails may be configured to fit in corresponding grooves in the bottom plate. The actuation screw may include a head having a drive recess and a shaft defining the helical cut. The helical cut may include a spiral cut that penetrates completely through the shaft and creates a fully open channel. The trial system may also include an articular insert trial attached to the top plate of the expandable tibial tray trial. The articular insert trial may include a piston with an annular groove configured to fit within a corresponding opening in the top plate such that a spring in the top plate snaps into the groove of the piston, thereby securing the articular insert trial to the expandable tibial tray trial. The system may also include a femoral trial having an anterior flange, a pair of posterior condylar flanges, and a distal portion therebetween. The femoral trial may have an outer articulating surface with a smooth rounded shape that contacts the articular insert trial and an inner surface shaped to match a resected femur with five resection cuts.

According to one embodiment, an expandable tibial tray trial includes top and bottom plates configured to nest together in a collapsed position, an actuation screw configured to rotate about an actuation axis, the actuation screw having a head and a shaft defining a helical cut, the head defining a plurality of indicators about its circumference, and an expansion ramp having a ramped body with a pair of vertical support walls defining a channel therebetween for receiving the actuation screw and a cross-pin extending across the channel and configured to pass through the helical cut of the actuation screw. When the actuation screw is rotated, the ramped body translates along the actuation axis and expands the top plate, thereby moving the top plate to an expanded position such that one of the indicators corresponds to a discrete height of the expanded trial.

The expandable tibial tray trial may include one or more of the following features. The indicators may include a series of numbers laser marked on the head of the actuation screw. The helical cut may include step portions, and when the cross-pin rests in one of the step portions, the visible indicator corresponds to one of the discrete heights. The bottom plate may have a central block portion defining a cylindrical through opening, and the actuation screw may be retained in the cylindrical through opening in the central block portion of the bottom plate. The block portion may define a gap in a top face of the block portion such that when one of the indicators aligns with the gap, a read-out of the indicator corresponds to the discrete height of the expanded trial. The head may define a transverse opening, which when aligned with the gap, indicates an initial starting position for the expandable trial.

According to one embodiment, an expandable tibial tray trial includes top and bottom plates configured to nest together in a collapsed position, an actuation screw configured to rotate about an actuation axis, the actuation screw having a head and a shaft defining a helical cut with step portions, and an expansion ramp having a ramped body with a pair of pins having free ends configured to engage the helical cut of the actuation screw. When the actuation screw is rotated, the pins ride along the helical cut and are configured to rest within one of the step portions, thereby ensuring that the expandable tibial tray trial expands only to discrete thicknesses.

The expandable tibial tray trial may include one or more of the following features. The ramped body may include a base with a closed bore sized and dimensioned to receive the actuation screw. The free ends of the pins may protrude into the bore such that they to ride along the helical cut when the screw is rotated. The pins may be off-axis and offset relative to one another. The helical cut of the actuation screw may be defined into the surface of the shaft without penetrating a core of the screw. The ramped body may define a plurality of male ramps with sloped surfaces configured to engage corresponding female ramp surfaces on the top plate.

According to one embodiment, a method for trialing an implant may include one or more of the following steps in any suitable order: (1) attaching a modular articular insert trial to an expandable trial, for example, via snap-fit or sliding attachment interface; (2) positioning the expandable trial in a surgical site, the expandable trial having top and bottom plates, an actuation screw having a helical cut with step portions separated by a thread rise, and an expansion ramp having a pin configured to ride along the helical cut; and (3) rotating the actuation screw to cause the expansion ramp to slide along the bottom plate and lift the top plate as the ramp translates forward, wherein when the pin rests in one step portion, the expandable trial is expanded to a discrete thickness. If the pin rests on the thread rise, the expandable trial cannot maintain its height under compression unless the step portion is reached. When the step portion is reached during expansion, the pin falls back into the step portion, thereby providing tactile feedback to the user. The actuation screw may have one or more visual indicators to designate a given trial thickness, thereby providing visual feedback to the user.

Also provided are kits including implants of varying types and sizes including femoral implants, tibial trays, and inserts that vary in anterior-posterior (AP) and/or medial-lateral (ML) aspects, trials including expandable tibial trials, articular trial inserts, and femoral trials, instruments of varying types and configurations including inserter instruments, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to trials, systems, and methods for knee replacement. In particular, knee arthroplasty trials may include an expandable tibial trial with a screw-driven ramp mechanism configured to create separation between top and bottom plates. The actuation screw may include stepped increments, which allow the trial to be set at distinct heights which correspond to available tibial insert sizes. The expandable tibial trial may include an articular insert trial, for example, which slides or snaps onto the expandable trial. In this manner, the total number of trials may be reduced and the efficiency of the trial reduction process may be improved by utilizing the expandable tibial trial, which represents multiple insert thicknesses.

Although generally described with reference to a knee arthroplasty, it will be appreciated that the trials and systems described herein may be applied to other orthopedic locations and applications, such as the spine including between vertebrae, long bones, such as a femur, a tibia, a humerus, a clavicle, a fibula, an ulna, a radius, bones of the foot, bones of the hand, or other suitable bone(s) or joints. It will further be appreciated that although generally described with reference to temporary trials, similar features may be applied to the permanent implants as well.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Figure 1:
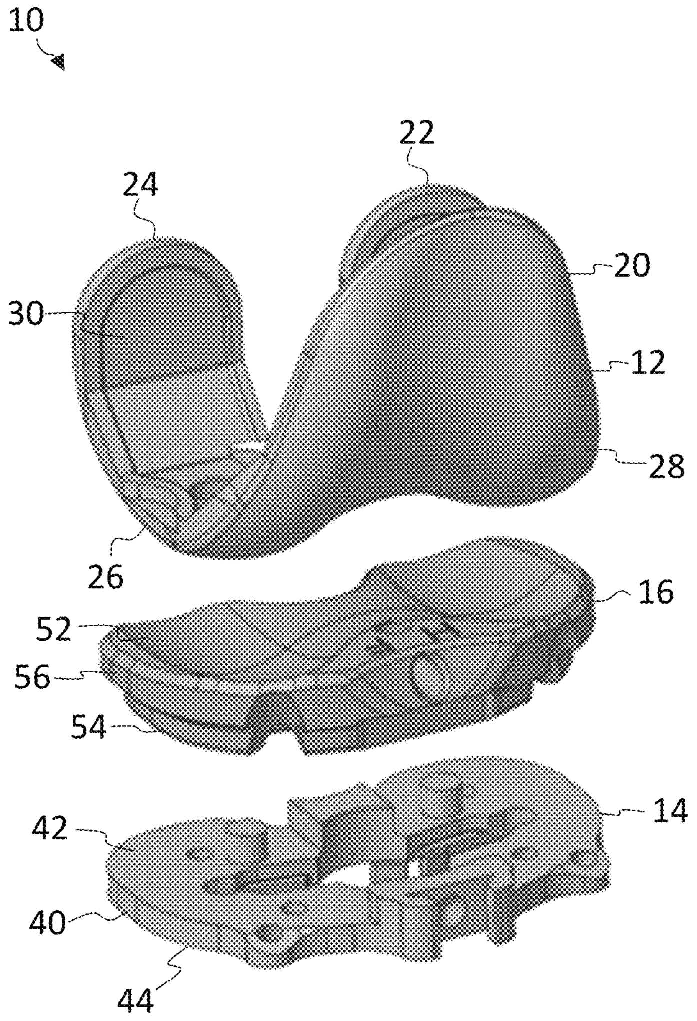
FIG. 1 shows an exploded view of a total knee arthroplasty trial including a femoral trial, a static tibial trial, and an articular insert trial according to one embodiment.

Turning now to the drawing, where like reference numerals may refer to like elements, FIG. 1 shows a total knee implant trial system 10 according to one embodiment. The total knee implant trial system 10 may include a trial femur or femoral trial 12, a trial tibia or tibial trial 14, and a trial insert or articular insert trial 16. The femoral trial 12 may be used to approximate a permanent femoral implant to replace the end of the femur or thigh bone, for example, after a resection. The tibial trial 14 may be used to approximate a permanent tibial tray implant to replace the end of the tibia or shin bone, for example, after a resection. In this embodiment, the tibial trial 14 is shown as a static component, but it will be appreciated that the tibial trial 14 may be substituted with any of the expandable trials 100, 200 described in more detail herein. The articular insert trial 16 is attachable to the tibial trial 14 and is configured to interface with the femoral trial 12 to mimic proper knee function. Each of the trials 12, 14, 16 are temporary components which match the geometry of final implants with corresponding sizes so that surgeons can evaluate the fit of a given size before permanently implanting the final implants in the patient.

The femoral trial 12 imitates the femoral implant, which curves over the front and back of the distal end of the femur to recreate the natural shape of an original femur for proper knee function. The femoral trial 12 may include an anterior flange 20, a pair of posterior condylar flanges 22, 24, and a distal portion 26 therebetween. The pair of posterior condylar flanges 22, 24 include a medial condyle portion 22 and lateral condyle portion 24 configured to mimic the condyles of a natural femur. An exterior or outer articulating surface 28 of the femoral trial 12 may form a rounded C-shape or other suitable shape corresponding to the natural distal femoral surface of a human knee. The femoral trial 12 may be positioned against a resected femur. For example, the femoral trial 12 may have an inner or interior surface 30 that is shaped to match with resection cuts on the distal end of the femur. In the embodiment shown, the interior surface 30 includes 5-cut bone interfacing surfaces, which mate with five corresponding resection cuts to ensure optimal fit. It will be appreciated that any suitable mating surface(s) for the resections may be used for the femoral trial 12 and corresponding femoral implant.

The tibial trial 14 imitates the tibial tray implant, which replaces the proximal end of the tibia or shin bone, for example, after a resection. The tibial tray 14 may be offered in multiple sizes that vary in the anterior-posterior (AP) and medial-lateral (ML) aspects in order to conform to patient anatomy. In this embodiment, the tibial trial 14 includes a plate 40 having opposite proximal and distal surfaces 42, 44. The distal surface 44 of the plate 40 is configured to engage the resected surface of the tibia. The proximal surface 42 is sized and shaped to receive or attach to the insert 16, for example, with one or more pegs or other securing mechanisms.

The insert trial 16 sits between the tibial trial 14 and the femoral trial 12 to mimic the motion of a natural knee and provide support as the knee is bent and flexed. The insert trial 16 includes a body with an upper articular surface 52 and an opposite lower surface 54 configured to mate with the tibial tray 14. The upper articular surface 52 may be recessed and contoured to articulate with the exterior articulating surface 28 of the femoral trial 12. An outer wall 56 of the insert 16 may have the general shape of a long oval indented at one side, such as a kidney-bean shape, which generally corresponds to the outer shape of the tibial trial 14. The insert 16 may be available in a number of thicknesses, for example, ranging from 10 mm to 30 mm. The insert 16 balances the joint space and provides articulating surface 52 as the knee goes through its physiologic range of motion.

Figure 2A:
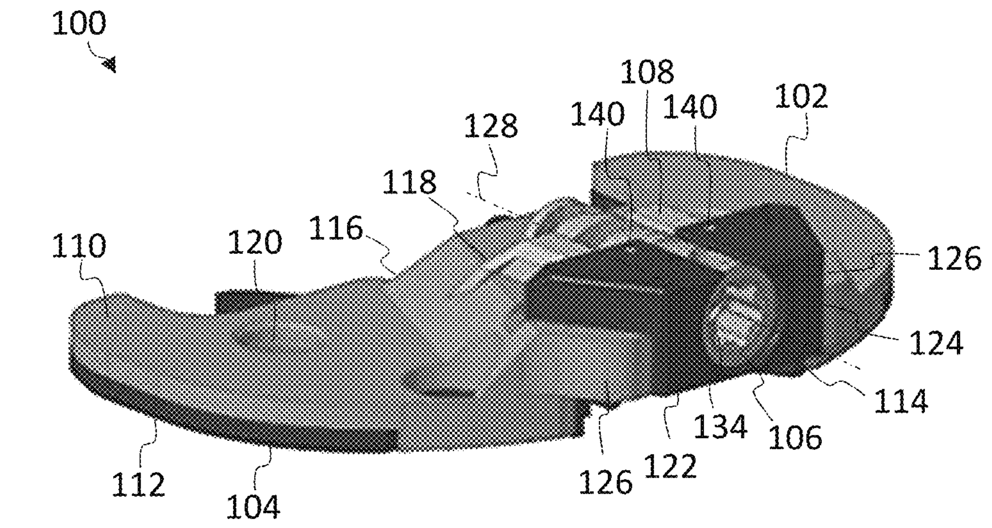
FIGS. 2A-2B show an expandable tibial trial assembly in fully collapsed and fully expanded positions, respectively, according to one embodiment.
Figure 2B:
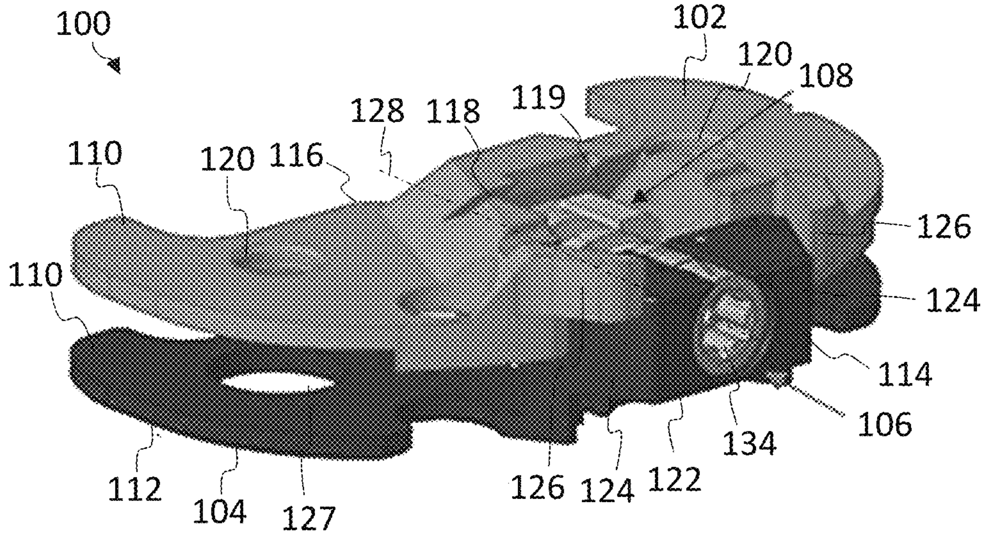

Turning now to FIGS. 2A-2B, an expandable tibial trial assembly 100 is shown according to one embodiment. The expandable trial assembly 100 includes top and bottom platforms or plates 102, 104, which are configured to expand via an expansion assembly including an actuation screw 106 and an expansion ramp 108. In FIG. 2A, the expandable tibial trial assembly 100 is shown in a fully collapsed position. As the screw 106 is rotated, the expansion ramp 108 is pushed forward between the two plates, 102, 104, thereby creating expansion therebetween. The ramp 108 slides along the bottom plate 104 and lifts the top plate 102 as the ramp 108 translates forward. In FIG. 2B, the expandable tibial trial assembly 100 is shown in a fully expanded position. The actuation screw 106 may be operated using a separate instrument, such as driver 400, located at the far anterior of the device 100. This anterior access enables the surgeon to expand the trial intraoperatively without removing it from the joint space. In one embodiment, the plates 102, 104 may be expanded at discrete increments matching thicknesses corresponding only to the available tibial insert thicknesses. The expandable tibial trial 100 may be expanded to the distinct thicknesses available, thereby allowing the surgeon to determine optimal sizing and fit for the permanent insert and tibial tray implants.

The top and bottom plates 102, 104 may be configured to nest together in the collapsed position, as best seen in FIG. 2A. The top and bottom plates 102, 104 each include an upper surface 110 and an opposite lower surface 112. When in the collapsed position, the bottom surface 112 of the top plate 102 may contact the top surface 110 of the bottom plate 104. The plates 102 each include an anterior side 114 configured to be accessed by the user and an opposite posterior side 116 positionable into the surgical site first. The outer profile of the plates 102, 104 may be rounded or curved, which is similar to a tibial tray implant. For example, the plates 102, 104 may have the general shape of a long oval indented at one side, for example, resembling a kidney-bean shape. The anterior side 114 may form an outer convex side as one long side and the posterior side 116 may include an inner concave side separating two lobes or wings.

The top plate 104 may include a complex recess 118 sized and dimensioned to receive at least a portion of the expansion ramp 108. The recess 118 may define an angled or ramped surface 119 which corresponds to the inclined plane 160 of the expansion ramp 108. When the expansion ramp 108 translates forward, the corresponding ramped surfaces 119, 160 slide against each other. The upward slope of the inclined plate 160 converts horizontal motion of the ramp 108 to vertical motion of the top plate 104, thereby causing the top plate 104 to lift vertically relative to the bottom plate 102. The top plate 104 may define one or more through openings 120 configured to connect the trial insert 180A, 180B to the expandable trial 100. The openings 120 may include cylindrical openings configured to receive corresponding posts 190 from snap-on insert trials 180A, 180B, for example, as described in more detail with respect to FIGS. 8A-8C.

The bottom plate 104 may include a central block portion 122 configured for retaining the actuation screw 106. The block portion 122 may be positioned centrally along the anterior side 114 of the bottom plate 104. The block portion 122 defines a cylindrical through opening sized and dimensioned to retain the actuation screw 106 therein. The sides of the block 122 may define sloped or slanted surfaces 124 configured to mate with projections 126 having corresponding mating surfaces along the top plate 102, thereby maintaining uniform vertical movement of the top plate 102 relative to the bottom plate 104. The projections 126 may extend anteriorly to mate with block surfaces 124. The projections 126 may be sloped or slanted inward and toward one another from the posterior side 116 to the anterior side 114 of the plate 102. The bottom plate 104 may define one or more through openings 127, which align with the post openings 120 in the top plate 102.

Figure 3:
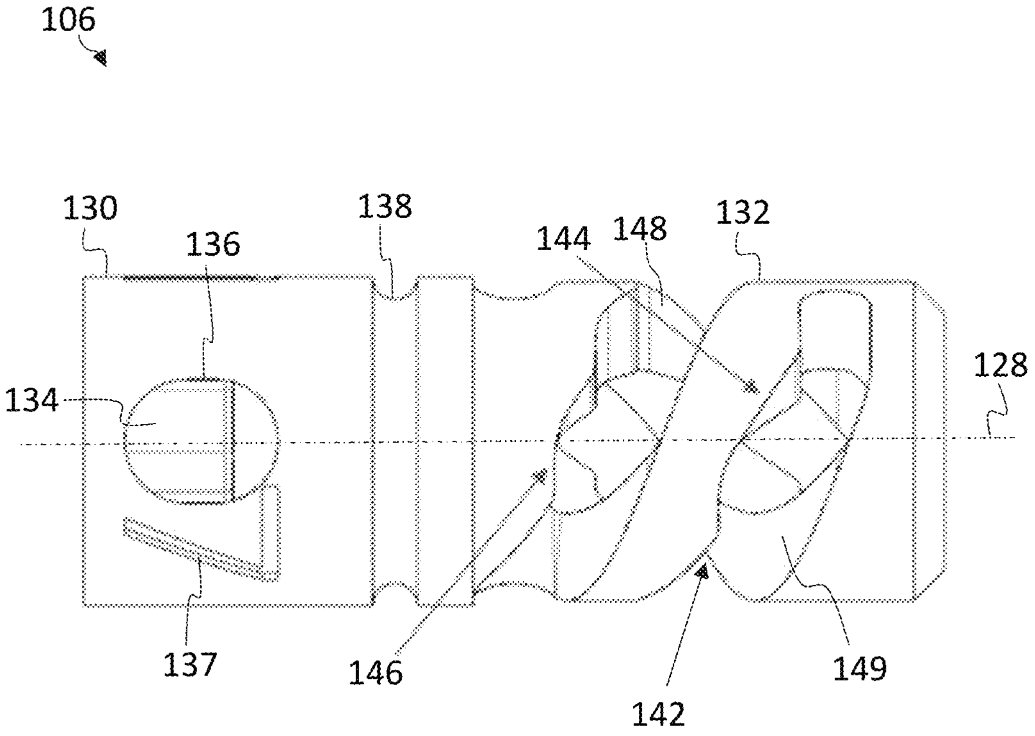
FIG. 3 shows a stepped helical screw with a step and thread rise for engaging an expansion ramp according to one embodiment.

The actuation screw 106 is configured to rotate about an actuation axis 128 between the anterior and posterior ends 114, 116 of the bottom plate 104. As best seen in FIG. 3, the actuation screw 106 includes a head 130 and a shaft 132. The proximal end of the head 130 may define a drive recess 134 configured to receive an instrument, such as driver 400, to rotate or actuate the actuation screw 106. The drive recess 134 may include a tri-lobe, hex, star, or other suitable recess configured to engage with the driver instrument to apply torque to the actuation screw 106. A transverse opening 136, for example, circular or obround opening, may be provided into the head 130 and in fluid communication with the drive recess 134. As described in more detail for FIG. 10, the transverse opening 136 may act as the zero indicator or starting position for the expansion heights available. The head 130 may also define a plurality of indicators 137, such as etching and/or laser markings, around its circumference, which provide the user a visual indication of the resulting heights as the screw 106 is rotated.

The actuation screw 106 may be retained in the bottom plate 104 by one or more pins 140, for example. The actuation screw 106 may define an annular groove 138 between the head 130 and shaft 132. The annular groove 138 may include a semi-circular recess configured to receive a portion of pins 140. For example, a pair of cylindrical pins 140 may extend vertically through the block 122 to retain the actuation screw 106 in the block 122 of the bottom plate 104, while still permitting rotation of the screw 106. It will be appreciated that the screw 106 may be constrained in the block portion 122 of the bottom plate 104 in any suitable manner.

In one embodiment, the actuation screw 106 is a stepped helical screw, which ensures that the trial device 100 expands only to distinct thicknesses that correspond to available tibial insert thicknesses. The shaft 132 of the actuation screw 106 defines a helical cut 142, which includes a spiral or helix-shaped channel cut along the length of the screw's body. The helical cut 142 penetrates completely through the shaft 132 and creates a fully open channel from the surface to the core of the shaft 132. The helical cut 142 is configured to receive and guide the cross-pin 152 of the expansion ramp 108. The helical cut 142 may include one or more thread rise portions 144 and one or more step portions 146. Each thread rise 144 connects the step portions 146. The thread rise 144 may include a curved or sloping relief, for example, having a larger radius than the step portions 146. As the screw 106 is rotated, the thread rise 144 correlates to the vertical distance the helical cut 142 advances axially. Due to the steep thread rise 144, the trial 100 cannot maintain its height under compression unless a step 146 has been reached. This prevents the user from setting the trial 100 to an in-between height for which no corresponding tibial insert is available. The step portions 146 may include curved or angled notches or cutouts, which are configured to retain the cross-pin 152 and correspond to the available tibial insert thicknesses. The step portion 146 may transition to the thread rise 144 via a pronounced ridge or crest. The thread rise 144 and stepped portions 146 may extend along one side 148 of the helical cut 142. The opposite side 149 of the helical cut may define a continuous helical or spiral curve. These sides 148, 149 may be reversed or otherwise configured for the stepped feature.

Figure 4A:
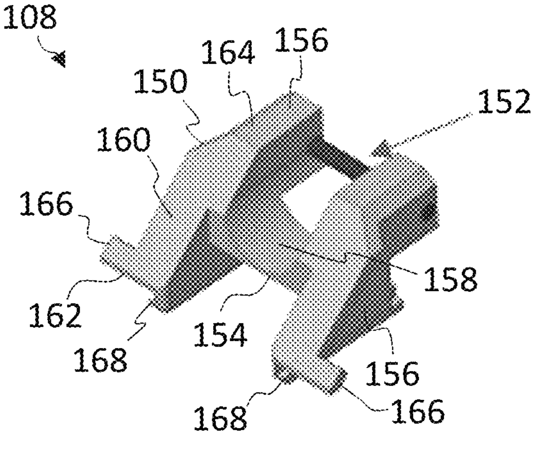
FIGS. 4A-4C show perspective, front cross-sectional, and side cross-sectional views, respectively, of the expansion ramp with a cross-pin configured to mate with the stepped thread of the actuation screw according to one embodiment.
Figure 4B:
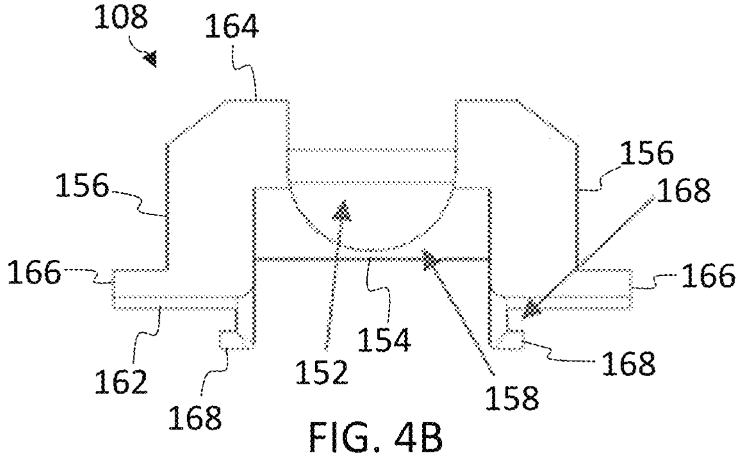
Figure 4C:
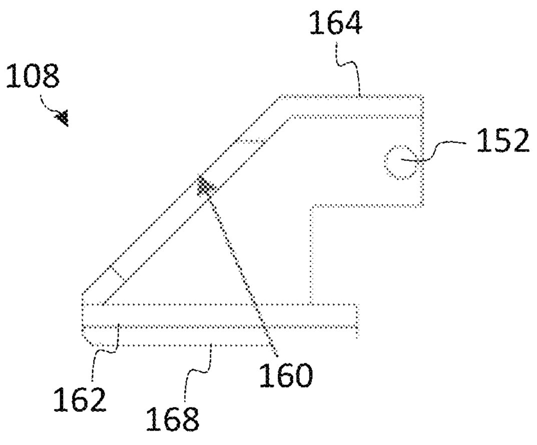

Turning now to FIGS. 4A-4C, the expansion ramp 108 is shown according to one embodiment. The expansion ramp 108 includes a ramped body 150 and a cross-pin 152 configured to engage the stepped helical screw 106. The ramped body 150 includes a base 154 and a pair of vertical support walls 156 defining an open channel 158 therebetween for receiving the body of the screw 106. The channel 158 includes a curved or semi-circular recess sized and dimensioned to provide clearance for the screw 106 therethrough. The central bore axis of channel 158 is coaxial with the actuation axis 128. The ramped body 150 defines a ramp or upper inclined plane 160 providing a sloped or slanted surface configured to guide or facilitate movement of the top plate 102. The inclined plane 160 may include a slope upward from a bottom surface 162 to a top surface 164 of the ramped body 150 to convert horizontal motion of the expansion ramp 108 to vertical motion of the top plate 102. The ramped body 150 may include a pair of lower wings 166 extending outward and away from one another along the bottom 162 of the ramped body 150. The wings 166 may provide the upper incline plane 160 with two separate L-shaped portions on opposite sides of the screw-receiving channel 158. A pair of rails 168 may extend from the bottom surface 162 of the ramped body 150. The rails 168 may have an L-shaped cross-section with free ends that extend outward and away from one another. The rails 168 are configured to fit in corresponding grooves in the bottom plate 104. In this manner, the rails 168 are configured to slide along the bottom plate 104 and provide linear movement of the ramped body 150 when the actuation screw 106 is rotated.

The expandable trial 100 may initially start at a first thickness, for example, equivalent to a 10 mm tibial insert trial. By using an instrument, such as driver 400, the actuation screw 106 may be rotated to expand the trial 100 to represent discrete thicknesses, for example, corresponding to 11 mm, 12 mm, 13 mm, 15 mm, and 17 mm tibial insert trials. As the stepped screw 106 rotates, it pushes the cross-pin 152 forward through the helical cut 142. The first step 146 may be encountered after the screw 106 has moved the cross-pin 152, and consequently the attached ramp 108, forward by a given distance, such as a 1 mm increment. The ramped surface 160 of ramp 108 may be inclined at a 45-degree angle, ensuring that the rise of the top plate 102 is equal to the run of the ramp 108 as it moves along the bottom plate 104. A similar increment, e.g., 1 mm increment, may occur when expanding from 11 mm to 12 mm and from 12 mm to 13 mm. When expanding from 13 mm to 15 mm, the step 146 in the screw 106 occurs after the cross-pin 152 has been pushed 2 mm by the screw 106. The same 2 mm step may be used when expanding from 15 mm to 17 mm. In other words, the amount of expansion is controlled by the location and number of steps 146 in screw 106, which allows for expansion to pre-determined trial thicknesses.

The stepped screw 106 ensures that the trial 100 expands only to distinct thicknesses that correspond to available tibial insert thicknesses. Due to the steep thread rise 144, the trial 100 cannot maintain its height under compression unless the next step 146 has been reached. This prevents the user from setting the trial to an in-between height for which no corresponding tibial insert is available. For example, steps 146 may not be present at 14 mm or 16 mm increments since those implant sizes are not offered. The steps 146 may incorporate a 3-degree back-angle to lock expansion while surgeons conduct range of motion testing. When a given step 146 is reached during expansion, the cross-pin 152 falls into the back-cut step 146, providing tactile feedback to the user. This allows the surgeon to feel that the expansion has reached an available implant size. In addition, the laser markings or indicators 137 around the periphery of the head 130 of the screw 106 provide visual feedback of the represented insert trial heights.

Figure 5A:
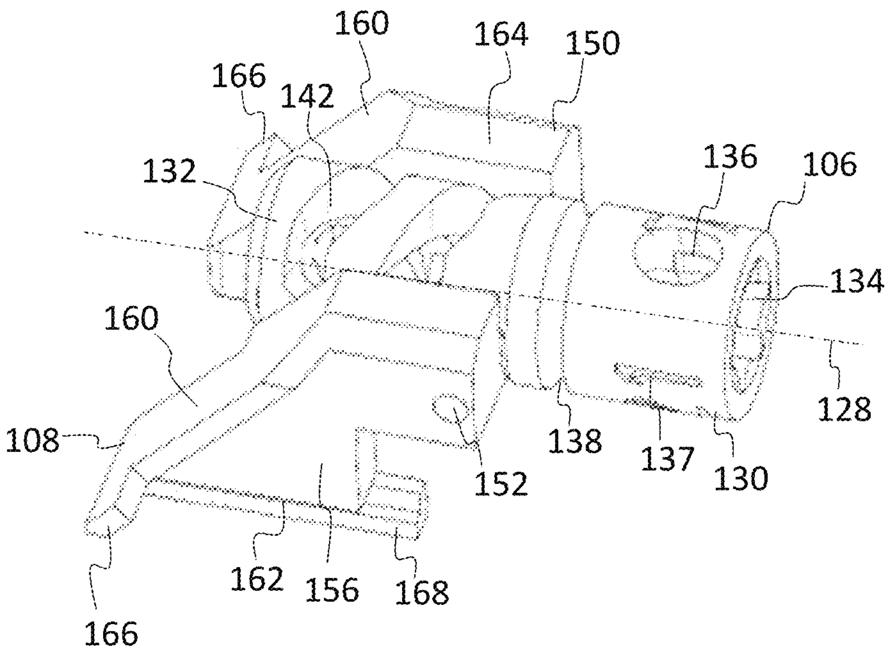
FIGS. 5A-5B show the actuation screw mating with the expansion ramp in collapsed and extended positions, respectively.
Figure 5B:
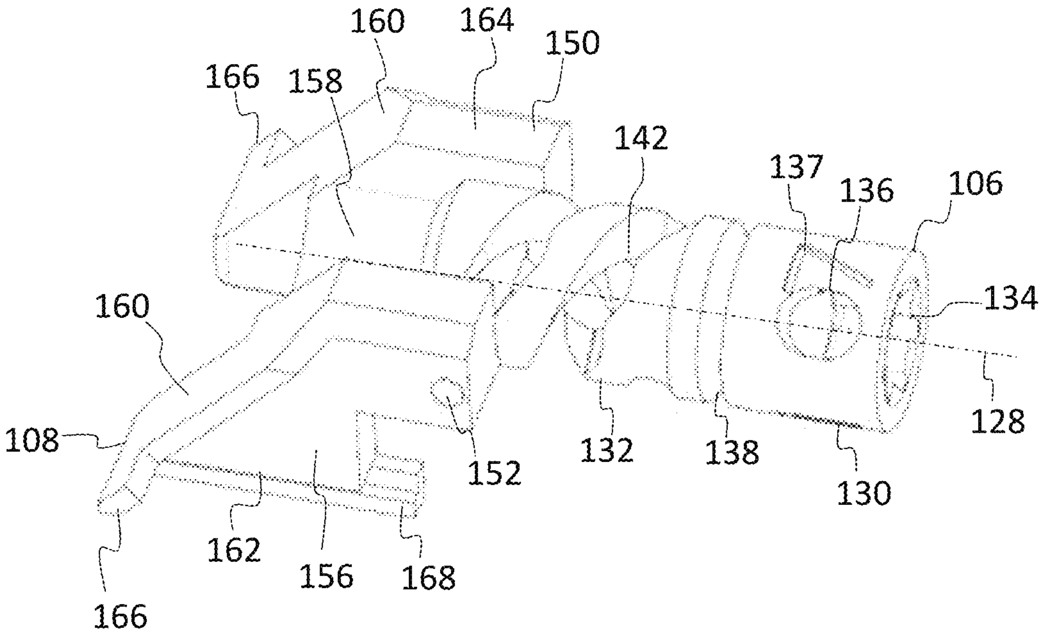
Figure 6A:
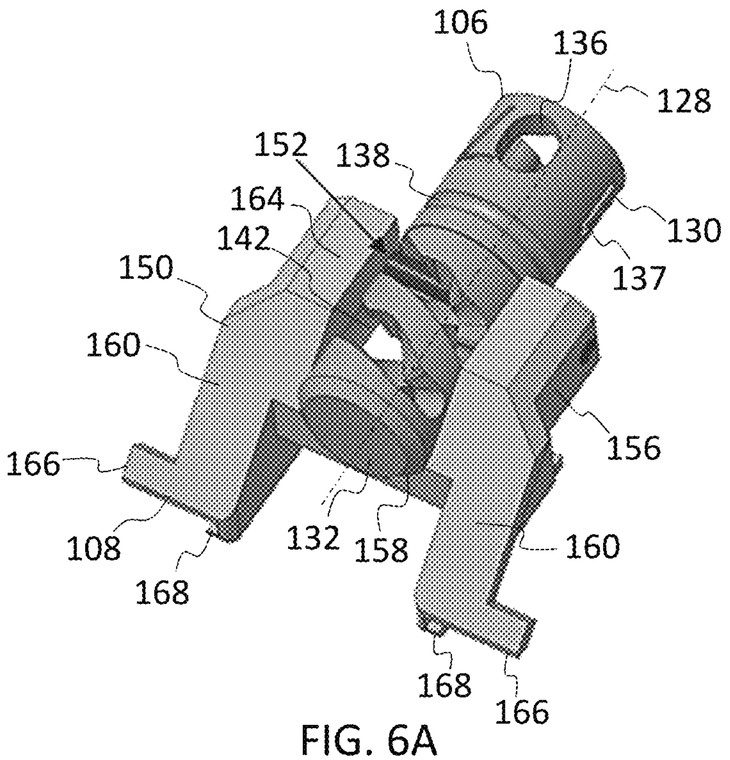
FIGS. 6A-6B show the screw ramp interface of the cross-pin in the collapsed and extended positions, respectively.
Figure 6B:
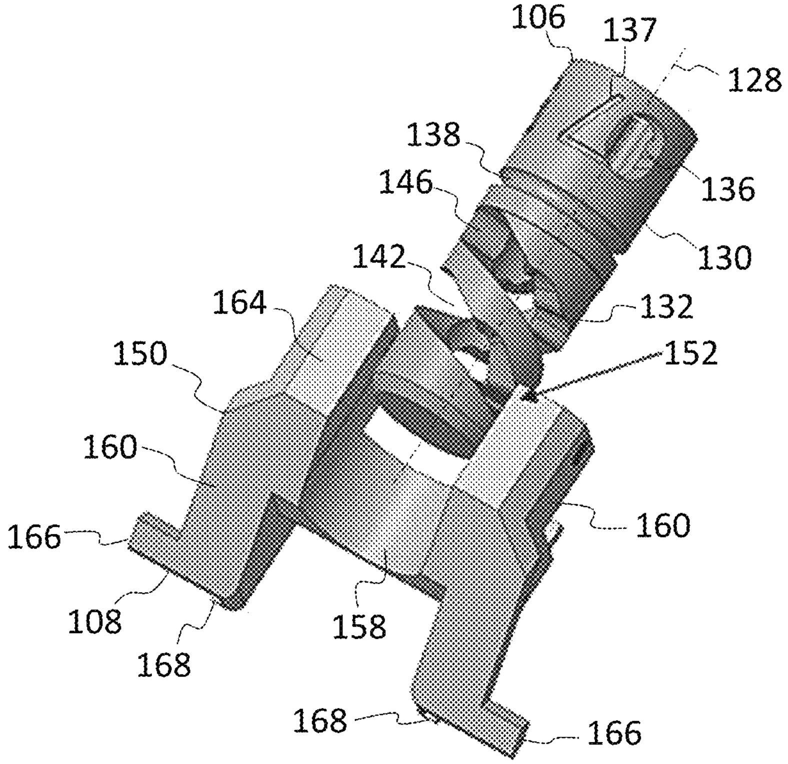
Figure 7A:
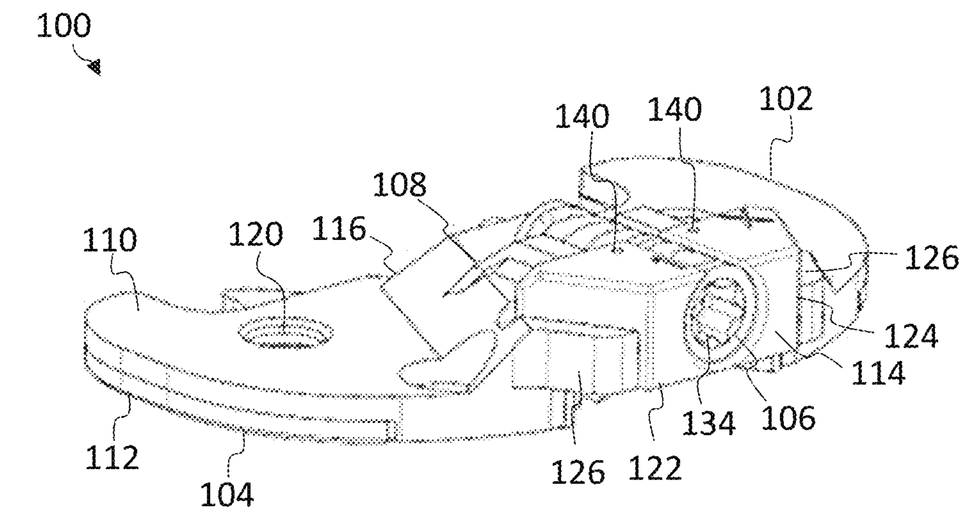
FIGS. 7A-7B show the tibial trial assembly in the collapsed and expanded positions, respectively.
Figure 7B:
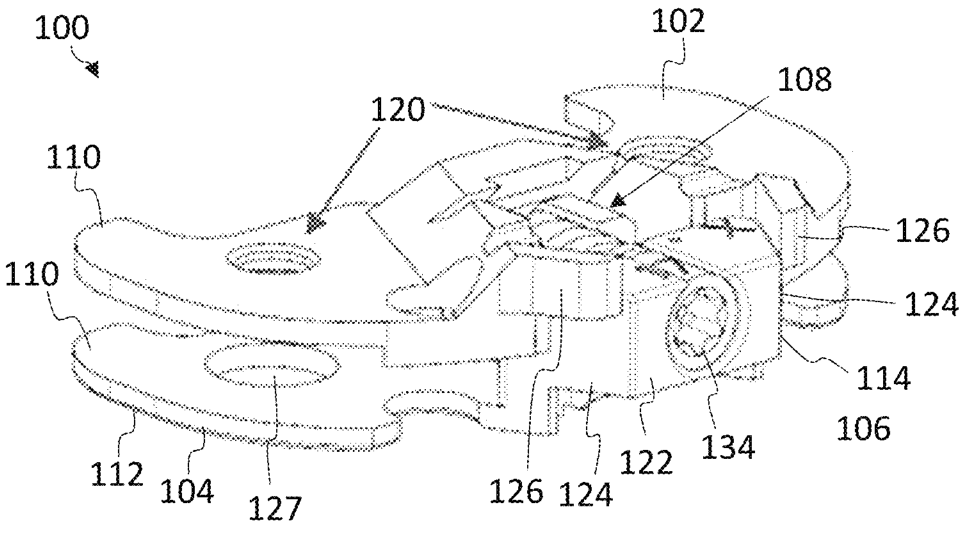

With emphasis on FIGS. 5A-5B and 6A-6B, movement of the expansion ramp 108 due to rotation of the actuation screw 106 is shown in more detail. In FIGS. 5A and 6A, the screw 106 and ramp 108 are shown in a collapsed position where the expansion ramp 108 is withdrawn to its most anterior position. The cross-pin 152 extends through the helical cut 142 of the screw 106 and rests in an initial starting position. In FIGS. 5B and 6B, the screw 106 and ramp 108 are shown in an extended position where the expansion ramp 108 is extending to its most posterior position. As the screw 106 rotates, the cross-pin 152 travels along helical cut 142 of the screw 106 until it reaches the final step 146. This, in turn, causes the ramped body 150 to slide along the bottom plate 104 due to rails 168, and forces inclined plane 160 against corresponding ramped surface 119 of the top plate 102, thereby causing the top plate 102 to expand upward. FIGS. 7A-7B show the expandable tibial trial 100 in the fully collapsed and expanded positions, respectively.

The expansion ramp 108 is captured by the bottom plate 104, restricting its movement to a single direction. This prevents tilting of the ramp 108 when the trial 100 is unevenly loaded. The expansion ramp 108 slides along the bottom plate 104 and elevates the top plate 102 as the ramp 108 moves forward. The top plate 102 is captured by the ramp 108, allowing expansion only when driven by the expansion ramp 108. This ensures that the trial 100 always remains at the height indicated by the laser marking 137 on the screw's head 130. The ramp 108 capturing the top plate 102 also prevents tilting of the top plate 102 when the trial 100 is loaded unilaterally. This expanding trial mechanism enables a single expansion mechanism to represent a number of different tibial insert thicknesses, for example, six different thicknesses, thereby simplifying the trialing process.

Figure 8A:
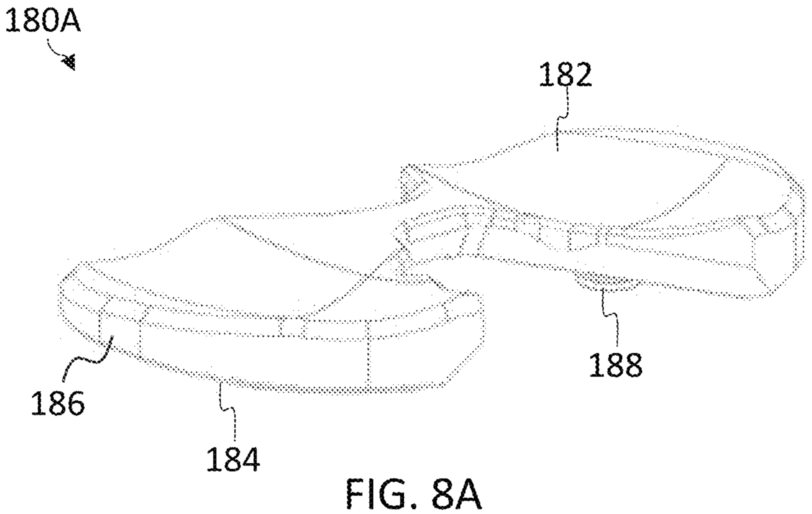
FIGS. 8A-8C show a cruciate retaining (CR) snap-on insert, which is attachable to the expandable tibial trial according to one embodiment.
Figure 8B:
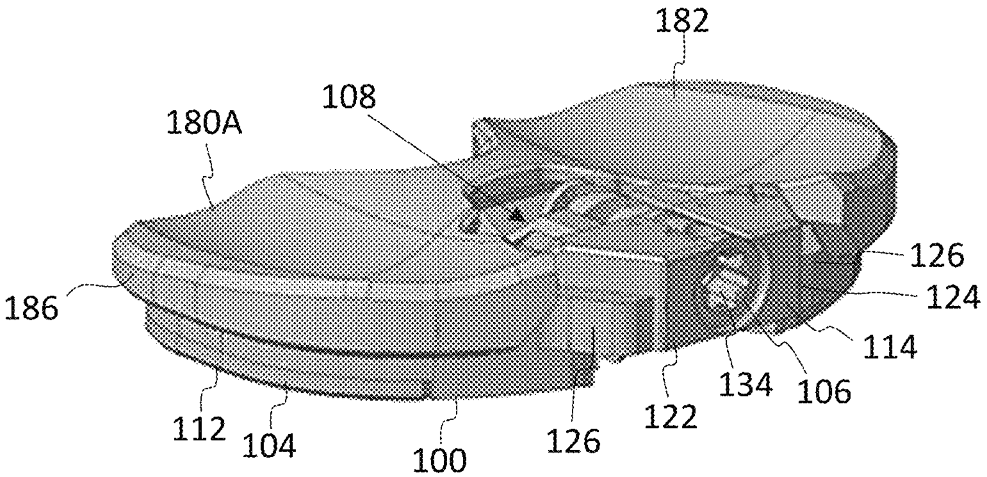
Figure 8C:
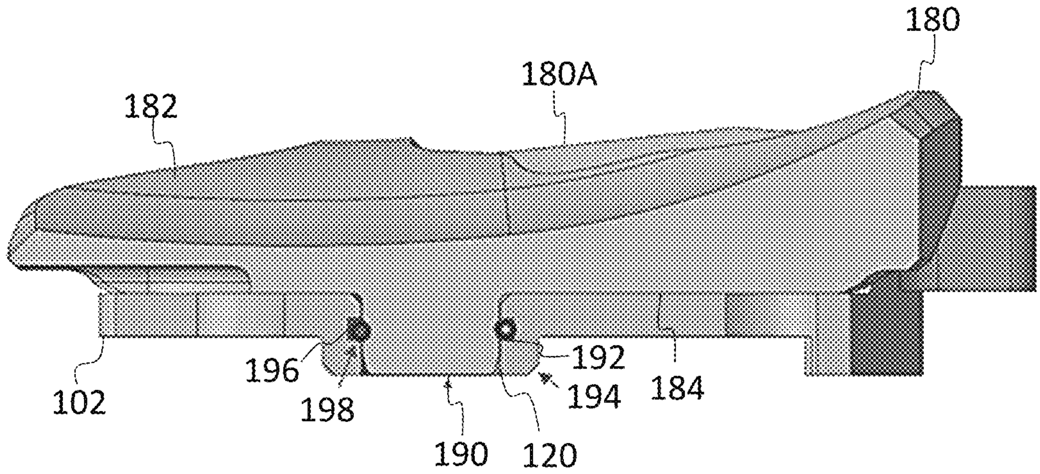
Figure 9A:
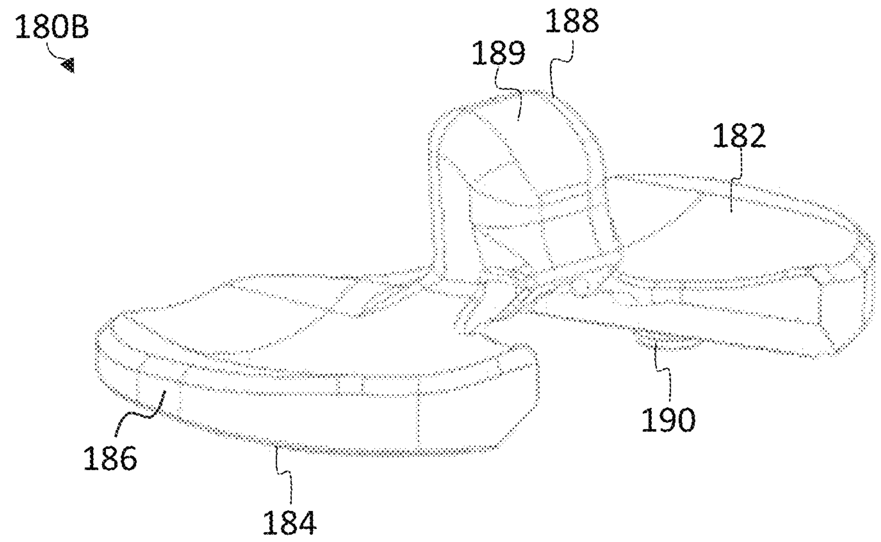
FIGS. 9A-9B show a posterior stabilized (PS) snap-on insert, which is attachable to the expandable tibial trial according to one embodiment.
Figure 9B:
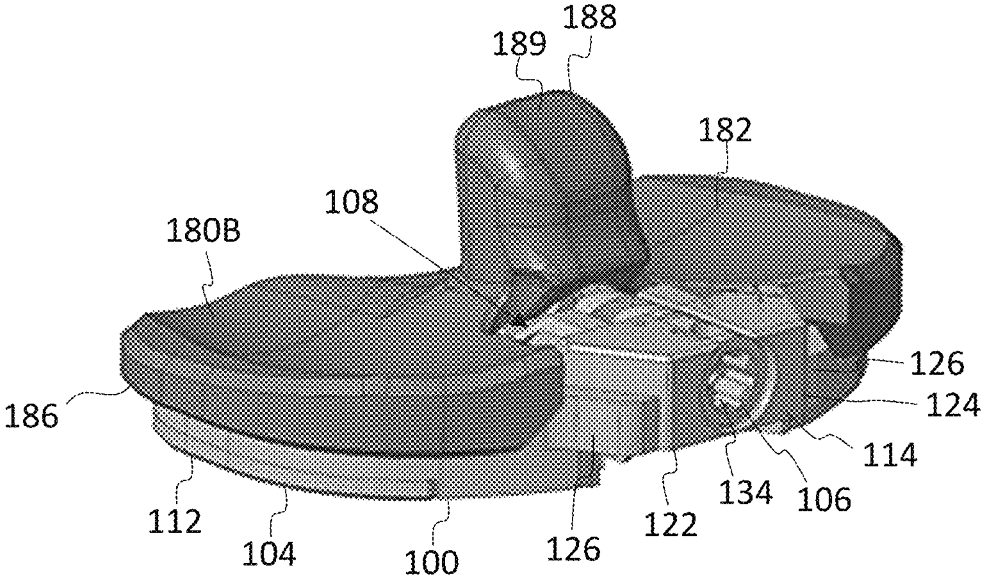

Turning now to FIGS. 8A-8C and 9A-9B, examples of modular articular insert trials 180A, 180B are shown. To minimize the number of components and enhance user-friendliness, the expandable tibial trial 100 may incorporate quick-connect articular insert trials 180A, 180B, for example, featuring a snap-on attachment interface. FIGS. 8A-8B show an articular insert trial 180A configured for trialing cruciate retaining (CR) implants. In cruciate retaining (CR) procedures, the posterior cruciate ligament (PCL) and inter-condyle of the femur are preserved, which may lead to better proprioception, balance, and kinematics. FIGS. 9A-9B show an articular insert trial 180B configured for trialing posterior stabilized (PS) implants. In posterior stabilized (PS) procedures, the posterior cruciate ligament (PCL) and inter-condyle of the femur are resected. The posterior stabilized (PS) implants include a raised surface or post 188 configured to fit into the femoral implant. The post 188 may have an articulating surface 189 configured to interface with the femoral implant, which may lead to better knee flexion and reliable restoration of the knee kinematics.

Insert trials 180A, 180B may be similar to insert trial 16. In both cases, the modular insert trials 180A, 180B include a body with an upper articular surface 182 and an opposite lower surface 184 configured to attach to the expandable tibial trial 100. The upper articular surface 182 may be recessed and contoured to articulate against a corresponding femoral trial. An outer wall 186 of the insert 180A, 180B may have a similar general outer shape as the expandable tibial trial 100. As shown in FIG. 9A-9B, the posterior-stabilized (PS) insert 180B may further include elevated post 188 extending from the upper articular surface 182. The elevated post 188 may be configured to fit in a corresponding box or notch in the middle of the femoral component. The insert trials 180A, 180B may have a known thickness to allow for determination of corresponding insert thicknesses from the read-out on the actuation screw indicators 137.

As best seen in FIG. 8C, one or more pegs or pistons 190 may extend from the insert trial 180A, 180B to couple the modular insert trial 180A, 180B to the expandable trial 100. The pistons 190 may include cylindrical posts having a round cross-section, which extend downward from the lower surface 184 of the insert 180. The pistons 190 are configured to fit within corresponding cylindrical openings 120 in the top plate 102 of the expandable trial 100. Each piston 190 may define an annular groove 192 configured to retain the piston 190 in the opening 120, for example, via spring 198. Each opening 120 may include a downward extension or housing 194 sized and dimensioned to be received in corresponding cylindrical opening 127 in the bottom plate 104 when the trial 100 is fully collapsed. The housing 194 defines an inner groove 196 configured to hold spring 198 therein. The spring 198 may include a seal spring, canted coil spring, snap ring, retaining ring, or other suitable securing mechanism.

When the piston 190 is fully seated in the openings 120, the spring 198 engages outer groove 192 in piston 190, thereby retaining piston 190 in top plate 102. The spring 198 may snap into the groove 192 and exert a radial force on the piston 190, thereby securing the modular insert trial 180A, 180B to the expandable trial 100. In one embodiment, each insert trial 180A, 180B may include a pair of pistons 190 that align with springs 198 housed in the top plate 102 of the expandable trial 100. The pistons 190 allow the insert trials 180A, 180B to securely attach to the expandable trial 100 while also facilitating easy coupling and decoupling. These modular articular insert trials 180A, 180B enable a single expansion trial 100 to be used for trialing both cruciate retaining (CR) and posterior stabilized (PS) insert styles. By employing one expansion trial 100 with two modular articular inserts 180A, 180B, it is possible to replace numerous static tibial insert trials.

Figure 10:
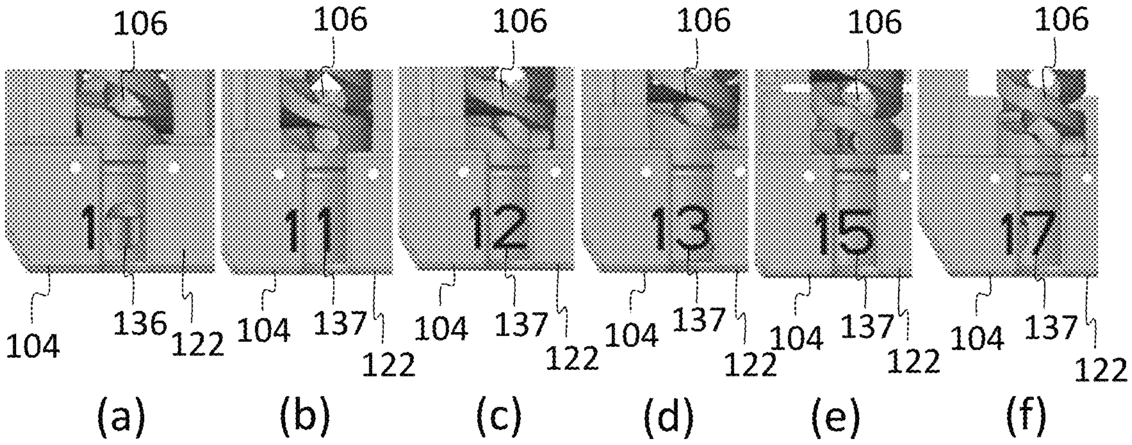
FIG. 10 shows laser marking indicators on the actuation screw for determining insert thickness according to one embodiment.

Turning now to FIG. 10, the actuation screw 106 is shown at a series of rotational positions, which indicate trial thicknesses to the user. The expandable trial 100 functions so that the surgeon can ascertain what thickness is currently being trialed during the procedure. The thickness of the trial 100 changes as it expands so the thickness reading also changes to indicate the resulting thickness. In one embodiment, the expandable trial 100 uses the method shown in FIG. 10 to read the resulting thickness. The number "1" is laser marked on the top face of the block portion 122 of the bottom plate 104 as that number is the same for all sizes (e.g., 10, 11, 12, 13, 15, 17). The second number 137 may be engraved and laser marked on the head 130 of the stepped screw 106. This allows the indicator number 137 to change as the screw 106 rotates. The indicator 137 directly ties the expansion of the trial 100 to the displayed thickness ensuring that the surgeon always knows what thickness the trial 100 is currently representing.

In the example shown in FIG. 10, at position (a), the opening 136 represents an initial starting position or implant size "10". When the screw 106 is rotated to position (b), indicator 137 aligns with a gap on a top face of the block 122 of bottom plate 104 to represent implant size "11". Similarly, when the screw 106 is further rotated, position (c) represents implant size "12", position (d) represents implant size "13", position (e) represent implant size "15", and position (f) represents implant size "17". It will be appreciated that any suitable trial and implant sizes may be represented on the trial 100 based on the given expansion. The stepped increments of the actuation screw 106 allow the surgeon to intraoperatively expand the trial 100 and set it to distinct heights, which correspond to the available tibial insert sizes.

Figure 11A:
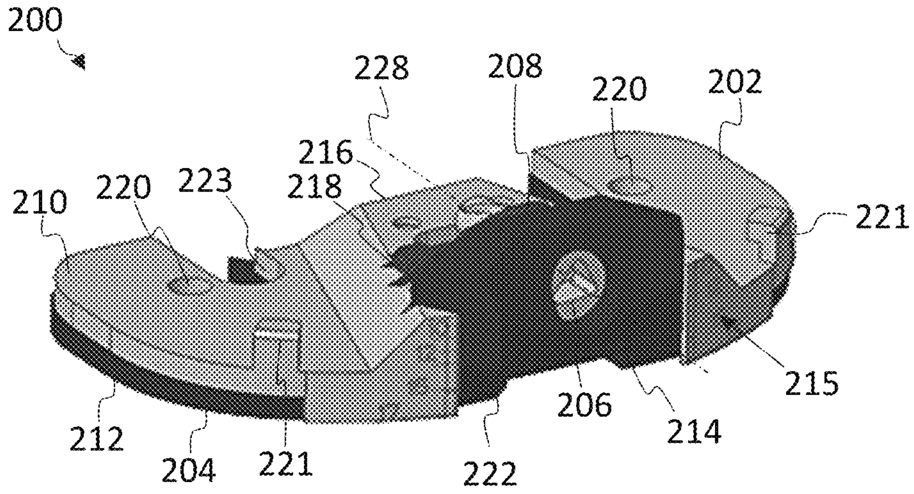
FIGS. 11A-11B show an expandable tibial trial assembly in fully collapsed and fully expanded positions, respectively, according to one embodiment.
Figure 11B:
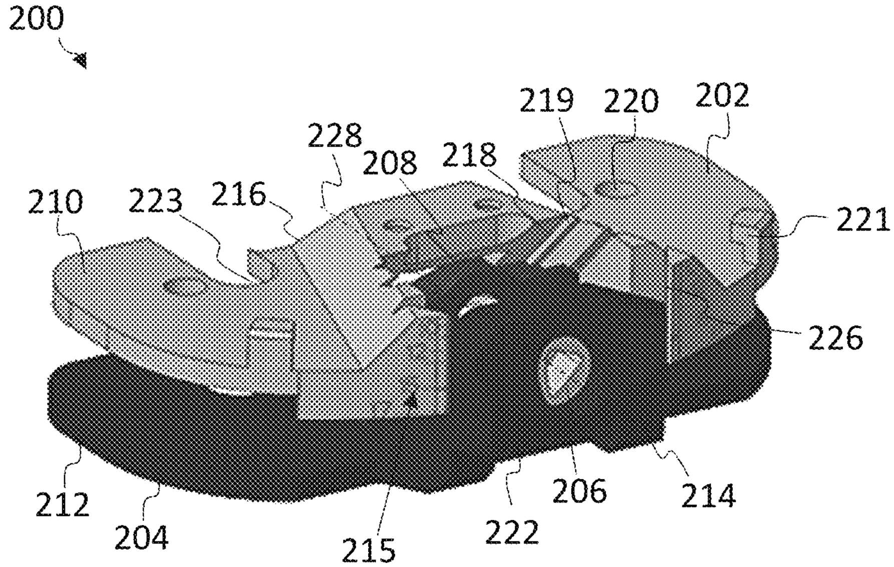

Turning now to FIGS. 11A-11B, an expandable tibial trial assembly 200 is shown according to another embodiment. Expandable trial assembly 200 is similar to expandable trial assembly 100 and includes top and bottom platforms or plates 202, 204, which are configured to expand via an expansion assembly including an actuation screw 206 and an expansion ramp 208. In this embodiment, the expansion assembly is modified with a stepped actuation screw 206 that mates with protruding pins 252 in the expansion ramp 208 to expand the top plate 202.

In FIG. 11A, the expandable tibial trial assembly 200 is shown in a fully collapsed position. As the actuation screw 206 is rotated, the expansion ramp 208 is pushed forward between the two plates, 202, 204, thereby creating expansion therebetween. The expansion ramp 208 slides along the bottom plate 204 and lifts the top plate 202 as the ramp 208 translates forward. In FIG. 11B, the expandable tibial trial assembly 200 is shown in a fully expanded position. In one embodiment, the plates 202, 204 may be expanded at discrete increments matching thicknesses corresponding to the available tibial insert thicknesses. In an alternative embodiment, the expandable tibial trial 200 may be adjusted to any height between the fully collapsed and expanded positions.

The top and bottom plates 202, 204 may be configured to nest together in the collapsed position, as best seen in FIG. 11A. The top and bottom plates 202, 204 each include an upper surface 210 and an opposite lower surface 212. When in the collapsed position, the bottom surface 212 of the top plate 202 may contact the top surface 210 of the bottom plate 204. The plates 202 each include an anterior side 214 configured to be accessed by the user and an opposite posterior side 216 positionable into the surgical site first. The outer profile of the plates 202, 204 may be rounded or curved in a manner similar to a tibial tray implant. For example, the plates 202, 204 may have the general shape of a long oval indented at one side, for example, resembling a kidney-bean shape. The anterior side 214 may form an outer convex side as one long side and the posterior side 216 may include an inner concave side separating two lobes or wings.

Figure 12A:
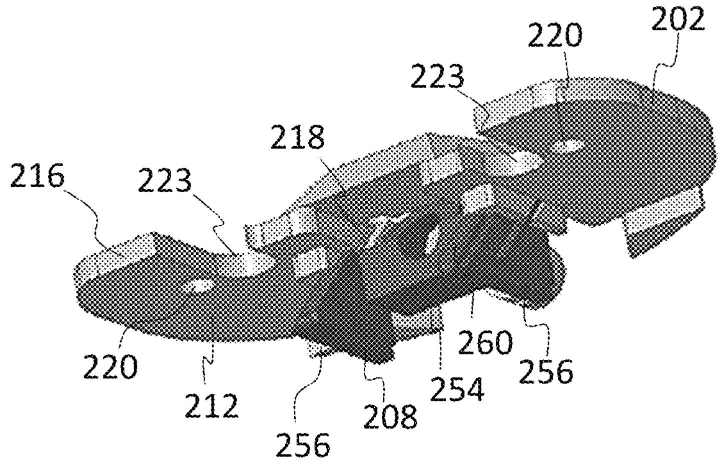
FIGS. 12A-12B show a perspective view of the top plate with the expansion ramp assembly and an underside view of the top plate according to one embodiment.
Figure 12B:
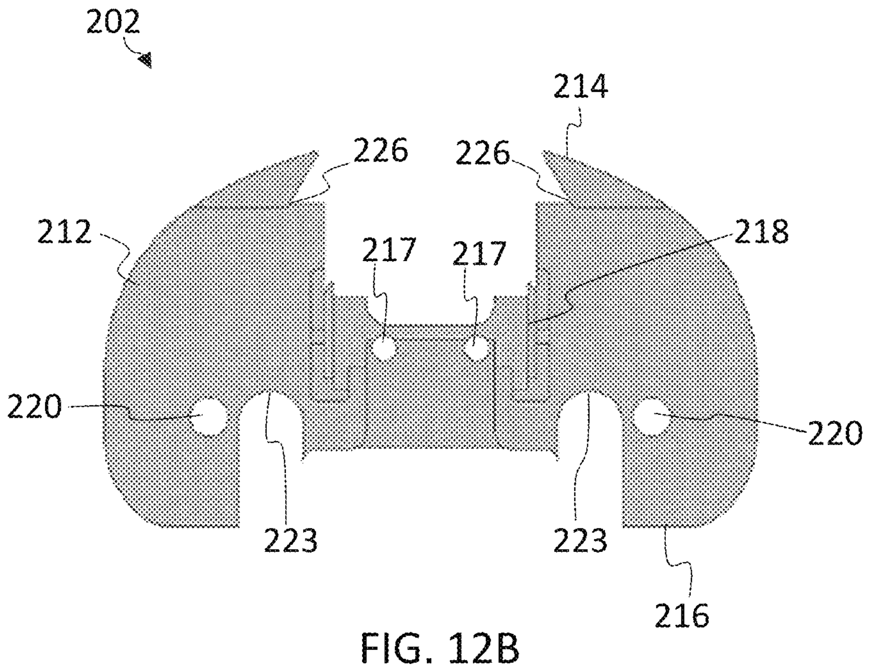

As best seen in FIGS. 12A-12B, the top plate 202 may include a complex recess 218 sized and dimensioned to receive at least a portion of the expansion ramp 208. The recess 218 may define a plurality of angled or ramped surfaces 219 which corresponds to the ramped surfaces 260 of the expansion ramp 208. When the expansion ramp 208 translates forward, the corresponding ramped surfaces 219, 260 slide against each other. The upward slope of the ramped surfaces 260 converts horizontal motion of the ramp 208 to vertical motion of the top plate 202, thereby causing the top plate 202 to lift vertically relative to the bottom plate 204.

Figure 19:
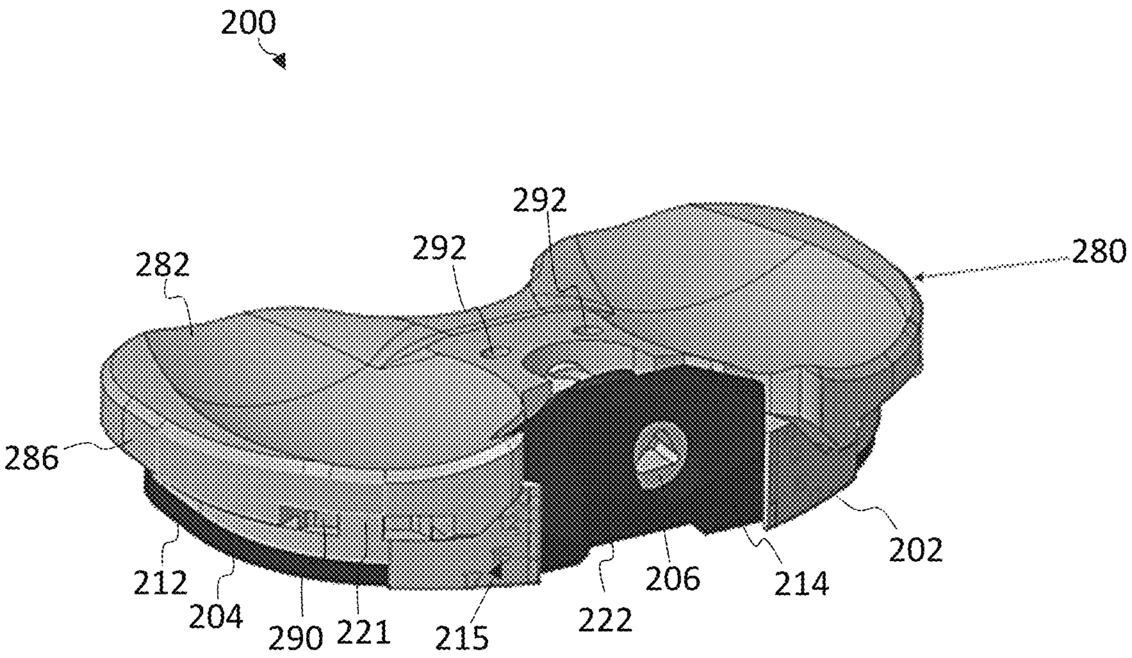
FIG. 19 shows a slide-on articular insert trial attached to the expandable tibial trial according to one embodiment.

The top plate 202 may define one or more clips 221 and through slots 223 configured to connect the trial insert 280 to the expandable trial 200. The clips 221 may include a pair of L-shaped extensions on the anterior side 214 of the top plate 202. The L-shaped clips 221 may extend upward from the top plate 202 and bend toward the posterior side 216 of the plate 202. The slots 223 may include a pair of elongated slots, which may be aligned substantially parallel to the actuation axis 228. The slots 223 may extend from the posterior side 216 of the top plate 202 and terminate at closed ends, for example, defining semi-circular recesses. As shown in FIG. 19, when the insert 280 slides into slots 223, the clips 221 secure the insert 280 to the top plate 202. It will be appreciated that sliding, snapping, or any other suitable attachment interface may be employed to temporarily attach the insert 280 to the top plate 202. The top plate 202 may also include bores 217 configured to align with bores 292 in the articular insert 280. The bores 217 may include a pair of vertical cylindrical bores 217 centrally positioned near the anterior side 216 of the top plate 202. Bores 217, 292 may be configured to receive a locking pin 300 for securing an optional modular posterior stabilized post, as described in more detail for FIGS. 20A-20B.

In this embodiment, the top plate 202 may include a plurality of indicators 215 along its anterior face 214. The indicators 215 may include a plurality of markings or etchings, for example, such as lines and numbers, that represent the corresponding heights of the tibial tray implants. The indicators 215 may be provided on both sides of the block 222 for better visibility as the top plate 202 moves relative to the bottom plate 204. When the top plate 212 is raised to an expanded position, the user may read the corresponding height from the corresponding indicator 215 to select the appropriate tibial tray implant.

Figure 13A:
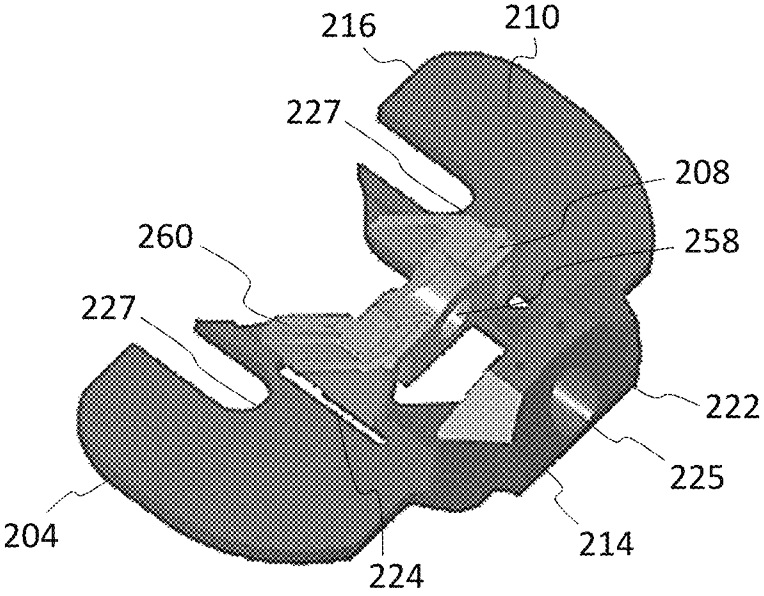
FIGS. 13A-13B show a perspective view of the bottom plate with the expansion ramp assembly and a top view of the bottom plate according to one embodiment.
Figure 13B:
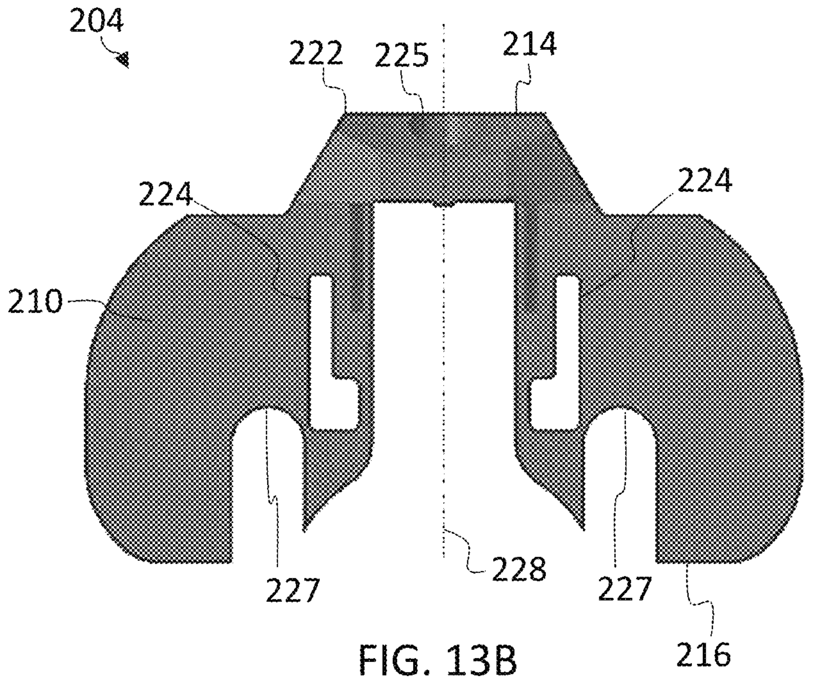

As best seen in FIGS. 13A-13B, the bottom plate 204 may include a central block portion 222 configured for retaining the actuation screw 206. The block portion 222 may be positioned centrally along the anterior side 214 of the bottom plate 204. The block portion 222 defines a cylindrical through opening 225 sized and dimensioned to retain the actuation screw 206 therein. The sides of the block 222 may mate with grooves 226 within the top plate 202, thereby maintaining uniform vertical movement of the top plate 202 relative to the bottom plate 204. The bottom plate 204 may define one or more slots 224, which guide the actuation ramp 208. The slots 224 may include a pair of elongated slots 224, which extend generally in parallel to actuation axis 228. The slots 224 may include an L-shaped cutout toward the posterior end of each slot 224. The bottom plate 204 may also include slots 227, which align with the corresponding slots 223 in the top plate 202.

Figure 14:
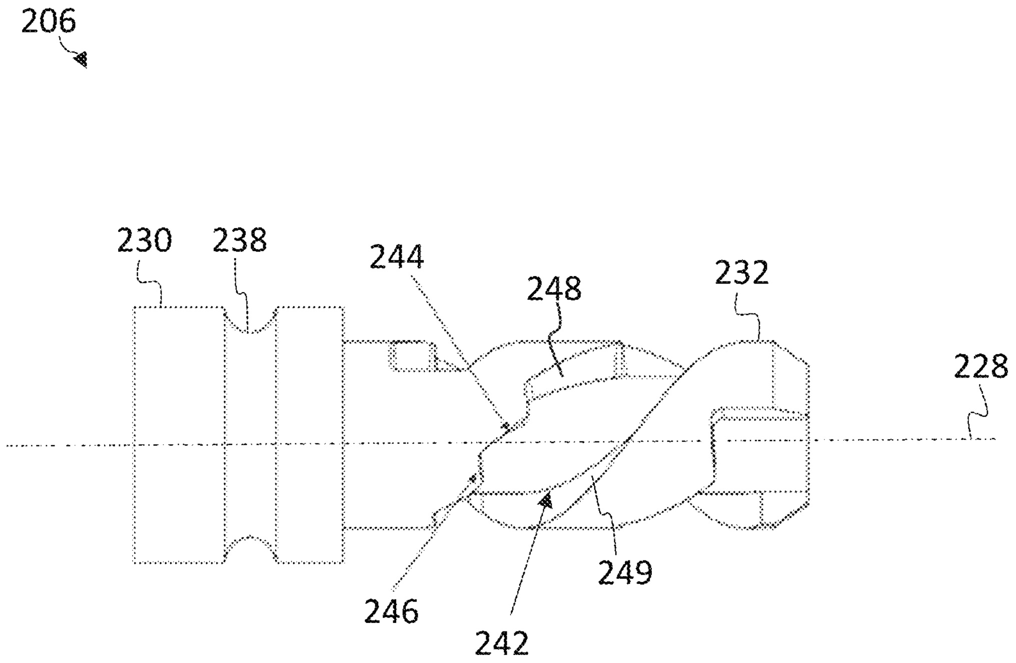
FIG. 14 shows a stepped screw with a step and thread rise according to one embodiment.

Turning now to FIG. 14, the actuation screw 206 is configured to rotate about an actuation axis 228 between the anterior and posterior ends 214, 216 of the bottom plate 204. Similar to actuation screw 106, actuation screw 206 includes a head 230 and a shaft 232. The proximal end of the head 230 may define a drive recess 234 configured to receive an instrument, such as a driver, to rotate or actuate the actuation screw 206. The drive recess 234 may include a triangle recess or other suitable recess configured to engage with a driver instrument, such as driver 400, to apply torque to the actuation screw 206. The actuation screw 206 may define an annular groove 238 between the head 230 and shaft 232. The annular groove 238 may include a semi-circular recess configured to receive a portion of securing pins, for example, as described for trial 100. The shaft 232 of the actuation screw 206 defines a helical cut 242, which includes a spiral or helix-shaped channel cut along the length of the shaft 232. The helical cut 242 may be defined into the surface of the shaft 232 with or without penetrating the core of the screw 206. The helical cut 242 may define a channel for the pins 252 to ride along, thereby guiding the pins 252 and movement of the expansion ramp 208.

In one embodiment, the actuation screw 206 is a stepped helical screw, which ensures that the device 200 expands only to distinct thicknesses that correspond to available tibial insert thicknesses. The helical cut 242 may include one or more thread rise portions 244 and step portions 246. Each thread rise 244 connects the step portions 246. The thread rise 244 is the vertical distance the helical cut 242 advances axially when the actuation screw 206 turns. The step portions 246 are configured to retain the pins 252 and correspond to the available tibial insert thicknesses. The stepped portion 246 may include, for example, an angled cut that forms an obtuse angle with the thread rise 244. The thread rise 244 and stepped portions 246 may extend along one side 248 of the helical cut 242. The opposite side 249 of the helical cut 242 may include a continuous helical or spiral curve. The stepped increments 246 of the screw 206 allow the surgeon to intraoperatively expand the trial 200 to discrete heights without removing it from the joint space. The trial 200 may be set to one of the distinct heights which correspond to the available tibial insert sizes. Because of the steep thread rise 244, the trial 200 cannot hold its height under compression if a step 246 has not been reached. This prevents the user from setting the trial 200 to an in between height, for which there is no available tibial insert. The steps 246 may also incorporate a slight back-angle to provide height stability when surgeons are conducting range of motion testing.

In an alternative embodiment, the actuation screw 206 is a continuous helix screw, which ensures the device 200 can expand to any suitable height along its range of motion. In this embodiment, both sides 248, 249 of the helical cut 142 may include a continuous spiraling groove without interruptions. The helix may be unbroken without any stepped areas providing for continuous adjustment to any desired height. In this manner, the user may adjust the trial height infinitely between a maximally contracted position and a maximally expanded position.

Figure 15A:
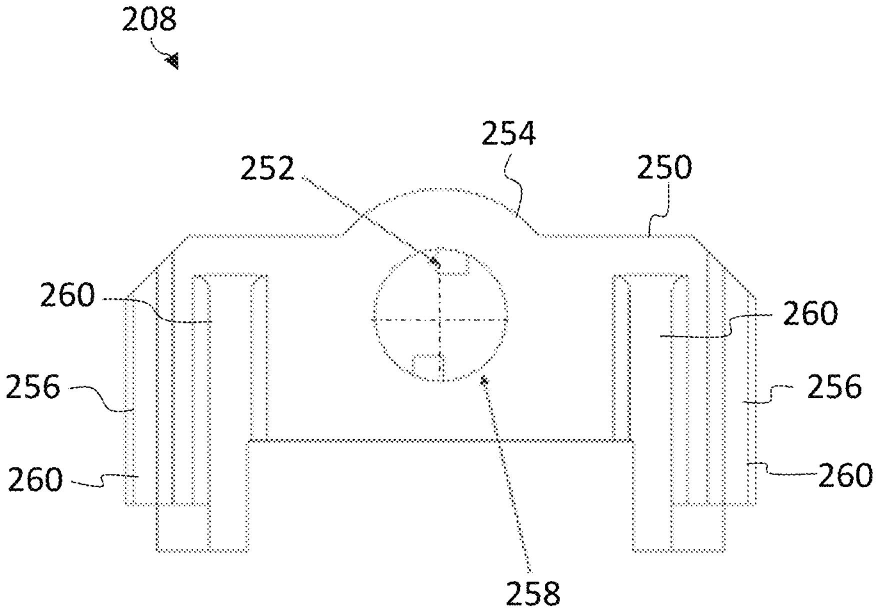
FIGS. 15A-15B show cross-sectional views of the expansion ramp with protruding pins configured to mate with the stepped thread of the actuation screw according to one embodiment.
Figure 15B:
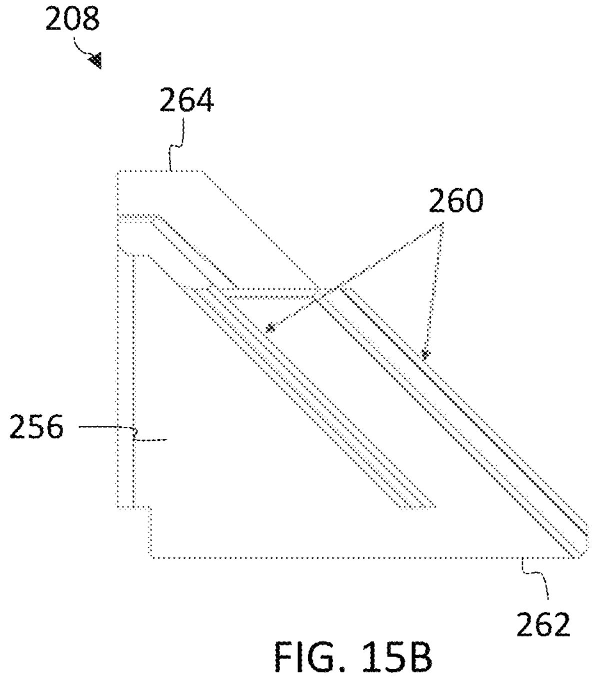

Turning now to FIGS. 15A-15B, the expansion ramp 208 is shown according to one embodiment. The expansion ramp 208 includes a ramped body 250 with protruding pins 252 configured to engage the stepped helical screw 206. The ramped body 250 includes a base 254 and a pair of vertical walls 256. The base 254 defines a bore 258 therethrough for receiving the body of the screw 206. The bore 258 may include a closed cylindrical opening sized and dimensioned to provide clearance for the screw 206 to pass therethrough. The central bore axis of bore 258 is coaxial with the actuation axis 228. The ramped body 250 defines a plurality of ramps 260 providing sloped or slanted surfaces configured to guide or facilitate movement of the top plate 202. The ramps 260 may include a slope upward from a bottom surface 262 to a top surface 264 of the ramped body 250 to convert horizontal motion of the expansion ramp 208 to vertical motion of the top plate 202. The ramps 260 may include male ramps, for example, having a dovetail or other mating configuration configured to fit with corresponding ramped surfaces in recess 218 in the top plate 202. The ramps 260 may include a pair of parallel ramps 260 located on different planes. For example, first and second pairs of ramps 260 may be located on opposite sides of the expansion ramp 208 to evenly lift the top plate 202.

The expansion ramp 208 includes one or more pins 252 which extend into the closed bore 258. The pins 252 may include a pair of protruding pins 252, for example, one at the top and one at the bottom of the bore 258, respectively. As best seen in FIG. 15A, the pins 252 may be offset relative to one another to ride along the edge 248 of the helical cut 242. The pins 252 may be laterally offset and off-axis from the central bore axis. The protruding free end of each pin 252 is receivable in the helical cut 242 in the actuation screw 206 to guide the expansion ramp 208 as the screw 206 rotates.

Figure 16A:
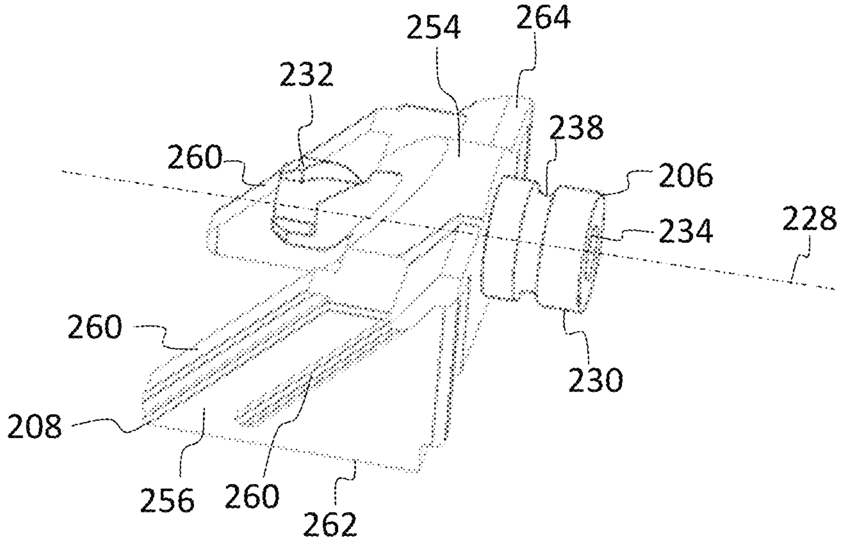
FIGS. 16A-16B show the actuation screw mating with the expansion ramp in collapsed and extended positions, respectively.
Figure 16B:
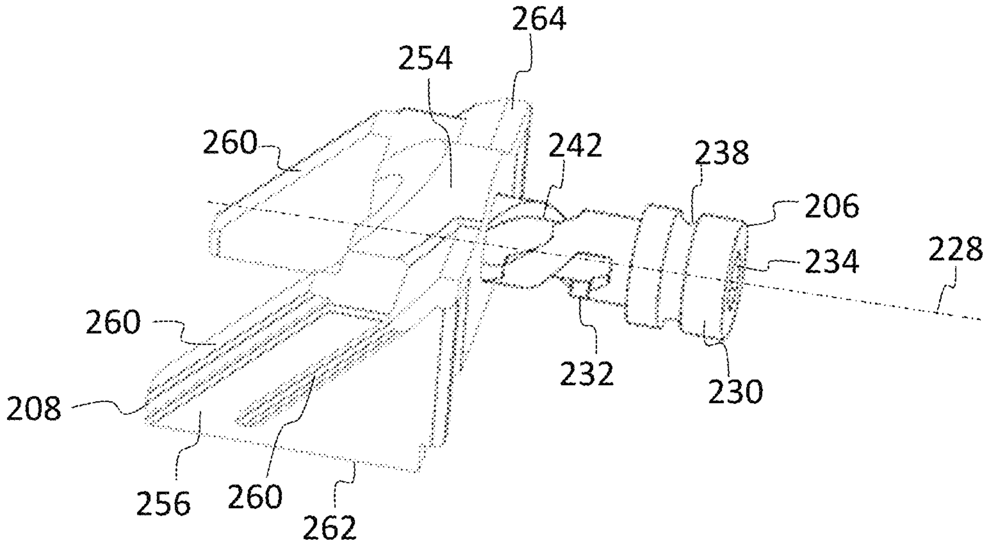
Figure 17A:
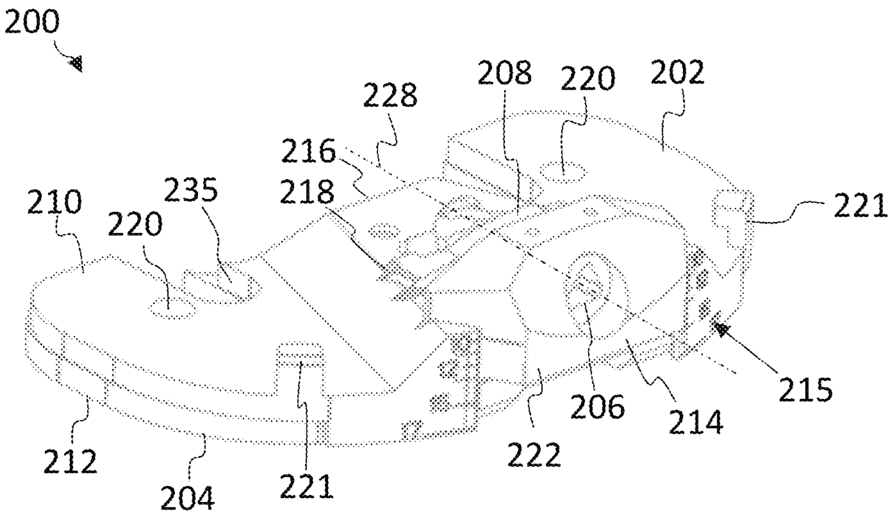
FIGS. 17A-17B show the tibial trial assembly in the collapsed and expanded positions, respectively.
Figure 17B:
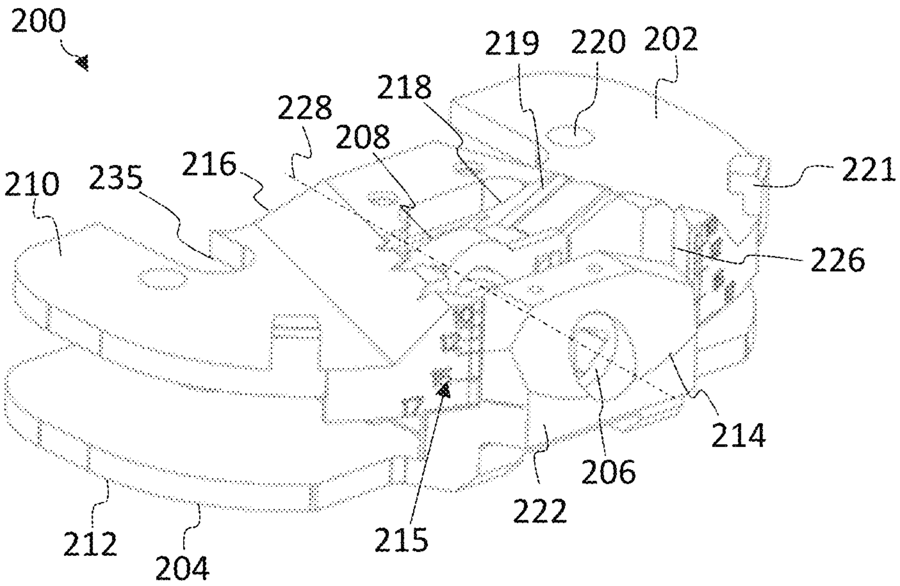

With emphasis on FIGS. 16A-16B, movement of the expansion ramp 208 due to rotation of the actuation screw 206 is shown in more detail. In FIG. 16, the screw 206 and ramp 208 are shown in a collapsed position where the expansion ramp 208 is withdrawn to its most anterior position. The pins 252 extend into the helical cut 242 of the screw 206 at an initial starting position. In FIG. 6B, the screw 206 and ramp 208 are shown in an extended position where the expansion ramp 208 is extending to its most posterior position. As the screw 206 rotates, the pins 252 travel along helical cut 242 of the screw 206 until they reach the final step 246. This, in turn, causes the ramped body 250 to slide along the bottom plate 204, and forces ramps 260 against corresponding ramped surfaces 219 of the top plate 202, thereby causing the top plate 202 to expand upward. FIGS. 17A-17B show the expandable tibial trial 200 in the fully collapsed and expanded positions, respectively.

Figure 18A:
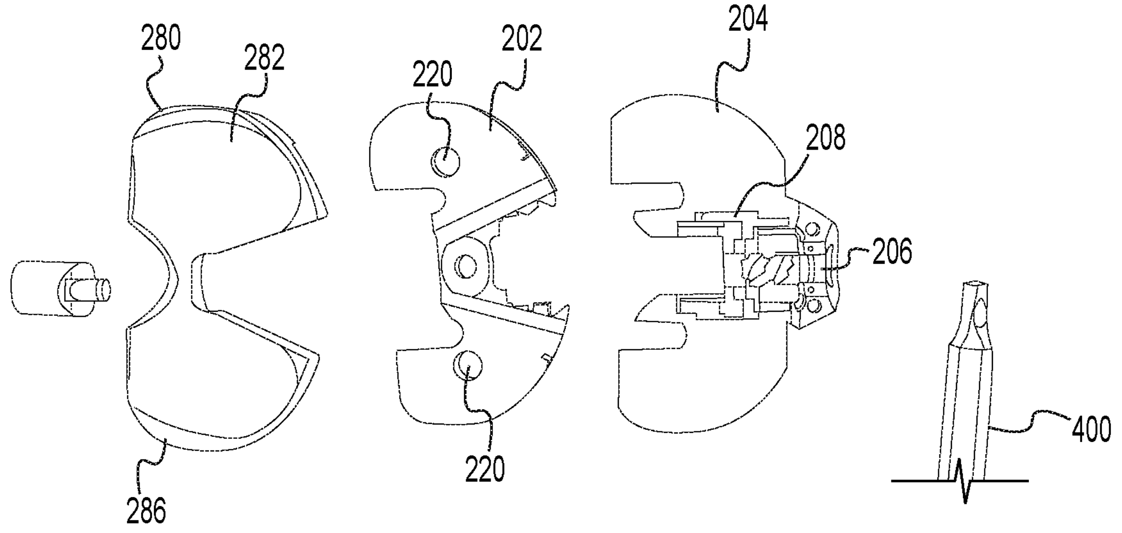
FIGS. 18A-18B show top and bottom views, respectively, of the articular insert trial, top and bottom plates, and expansion assembly of the expandable tibial trial according to one embodiment.
Figure 18B:
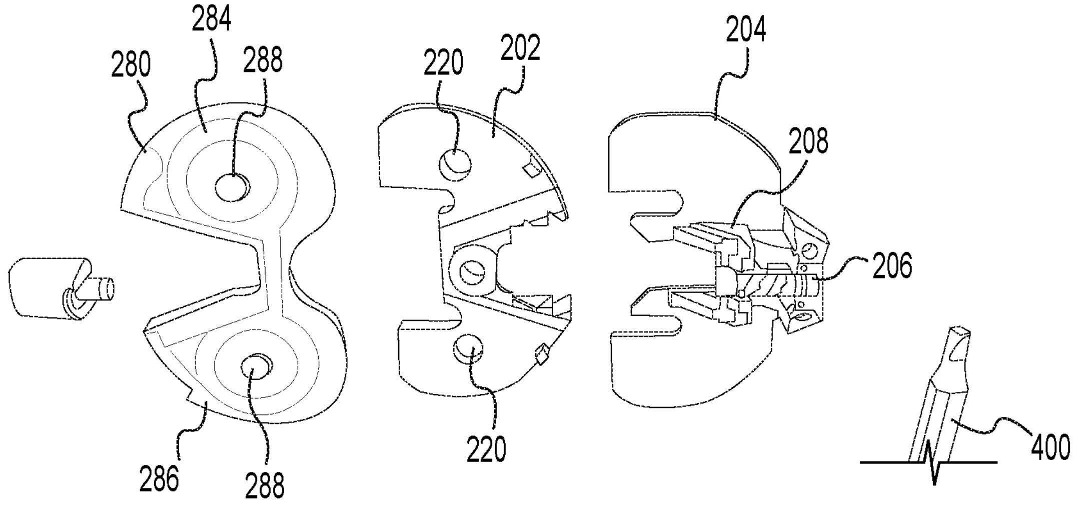

The articular insert 208 may be connected to the top plate 202, for example with a snapping or sliding interface. The insert 280 may include a body with an upper articular surface 282 and an opposite lower surface 284 configured to attach to the expandable tibial trial 200. The upper articular surface 282 may be recessed and contoured to articulate against a corresponding femoral trial, such as femoral trial 12. An outer wall 286 of the insert 280 may have a similar general outer shape as the expandable tibial trial 200. In the embodiment shown in FIGS. 18A-18B, one or more pegs or posts 288 may protrude from the lower surface 284 of the insert 280. The posts 288 are configured to fit in the corresponding openings 220 in the top plate 202, thereby securing the insert 280 to thereto. In the embodiment shown in FIG. 19, the articular insert 280 includes a slide-on attachment interface. The articular insert 280 slides along slots 223 in the top plate 202 and clips 221 secure the insert 280 to the top plate 202. For example, the clips 221 hook into grooves 290 along the outer wall 286 of the insert 280, thereby temporarily securing the articular insert 280 to the expandable trial 200.

Figure 20A:
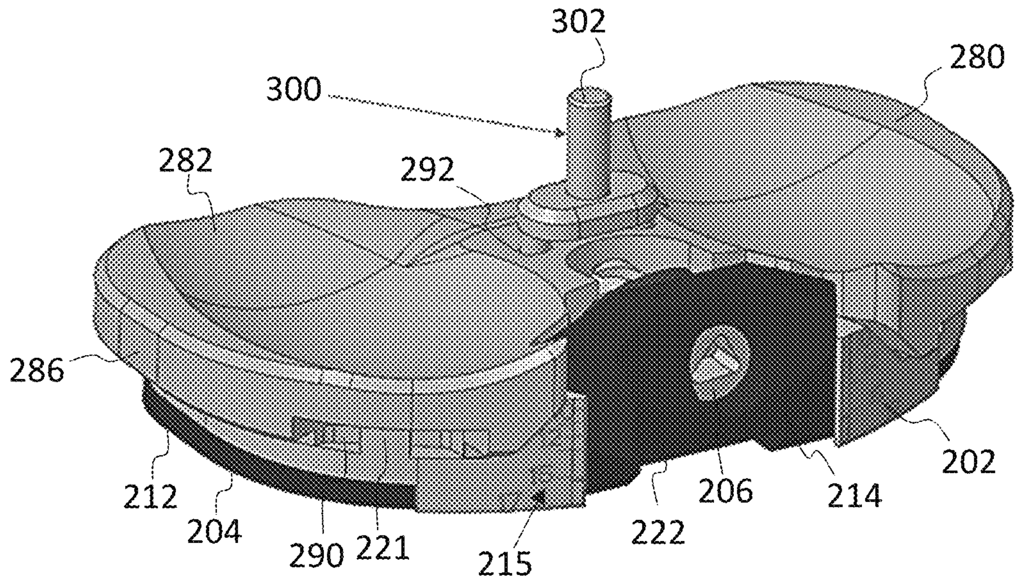
FIGS. 20A-20B show the articular insert trial and expandable tibial trial assembly with a locking pin for attaching a modular posterior stabilized (PS) post according to one embodiment.
Figure 20B:
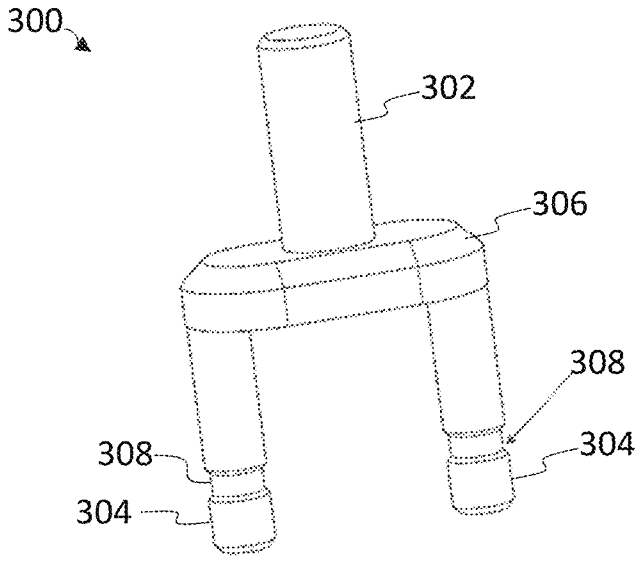

With further emphasis on FIGS. 20A-20B, a modular posterior stabilizing (PS) post may be incorporated with the articular insert 280 in order to easily provide the option to use a posterior stabilized femur implant. The modular post may be attached to the articular insert 280 with a locking pin 300, for example. As best seen in FIG. 20B, the locking pin 300 may include a central cylindrical post 302, a pair of cylindrical legs 304, and a bridge portion 306 connecting the central post 302 and legs 304. The post 302 may be configured to extend vertically upward to receive the modular post (for example, similar to post 188) and the legs 304 may extend vertically downward from the bridge portion 306 to fit into the articular insert 280. The articular insert 280 may define a pair of bores 292, which align with corresponding bores 217 in the top plate 202 of the expandable trial 200. Each leg 304 may define an annular groove 308 near its free end for snap-on engagement with the articular insert 280. Similar to piston 190, the groove 308 may be configured to receive a spring to provide a temporary connection to the trial assembly, which is stable under load but can be readily removed.

In the embodiments described herein, the trials are expandable, which decrease the overall count of instruments and improve efficiency during the trial reduction process. Unlike static systems, the expandable trials do not have multiple components, which need to be forced repeatedly in or out of the joint space. Instead, a single trial can be inserted and expanded to the desired height, thereby reducing component count, improving speed of the procedure, and enhancing ease or use. The expandable trial allows the surgeon to easily find the appropriate insert thickness by changing between sizes with a single twist of the driver. The stepped screw also controls expansion and allows the trial to lock only at desired expansion heights. The stepped screw may simultaneously provide the user with tactile and/or visual feedback corresponding to the trial thickness.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A knee arthroplasty trial system comprising:

an expandable tibial tray trial having top and bottom plates, an actuation screw retained in the bottom plate, and an expansion ramp configured to slide along the bottom plate and lift the top plate as the ramp translates forward, wherein the actuation screw defines a helical cut with step portions, and the expansion ramp includes a pin configured to engage the helical cut of the actuation screw, and wherein when the actuation screw is rotated, the pin rides along the helical cut and is configured to rest within one of the step portions, thereby ensuring that the expandable tibial tray trial expands only to discrete thicknesses.

2. The system of claim 1, wherein the expansion ramp includes a ramped body with a pair of vertical support walls defining a channel therebetween for receiving the actuation screw.

3. The system of claim 2, wherein the pin is a cross-pin extending between the pair of vertical support walls and across the channel.

4. The system of claim 2, wherein the ramped body defines an upper inclined plane providing a sloped surface configured to mate with a corresponding surface on the top plate.

5. The system of claim 2, wherein the ramped body includes a pair of rails extending from a bottom surface of the ramped body, wherein the rails are configured to fit in corresponding grooves in the bottom plate.

6. The system of claim 1, wherein the actuation screw includes a head having a drive recess and a shaft defining the helical cut.

7. The system of claim 6, wherein the helical cut includes a spiral cut that penetrates completely through the shaft and creates a fully open channel.

8. The system of claim 1 further comprising an articular insert trial attached to the top plate of the expandable tibial tray trial.

9. The system of claim 8, wherein the articular insert trial includes a piston with an annular groove configured to fit within a corresponding opening in the top plate such that a spring in the top plate snaps into the groove of the piston, thereby securing the articular insert trial to the expandable tibial tray trial.

10. The system of claim 8 further comprising a femoral trial having an anterior flange, a pair of posterior condylar flanges, and a distal portion therebetween, the femoral trial has an outer articulating surface with a smooth rounded shape that contacts the articular insert trial and an inner surface shaped to match a resected femur with five resection cuts.

11. An expandable tibial tray trial comprising:

top and bottom plates configured to nest together in a collapsed position;

an actuation screw configured to rotate about an actuation axis, the actuation screw having a head and a shaft defining a helical cut, the head defining a plurality of indicators about its circumference; and an expansion ramp having a ramped body with a pair of vertical support walls defining a channel therebetween for receiving the actuation screw and a cross-pin extending across the channel and configured to pass through the helical cut of the actuation screw, wherein when the actuation screw is rotated, the ramped body translates along the actuation axis and expands the top plate, thereby moving the top plate to an expanded position such that one of the indicators corresponds to a discrete height of the expanded trial.

12. The expandable tibial tray trial of claim 11, wherein the indicators include a series of numbers laser marked on the head of the actuation screw.

13. The expandable tibial tray trial of claim 11, wherein the helical cut includes step portions, and when the cross-pin rests in one of the step portions, the visible indicator corresponds to one of the discrete heights.

14. The expandable tibial tray trial of claim 11, wherein the bottom plate has a central block portion defining a cylindrical through opening, and the actuation screw is retained in the cylindrical through opening in the central block portion of the bottom plate.

15. The expandable tibial tray trial of claim 14, wherein the bottom plate defines a gap in a top face of the block portion, and when one of the indicators aligns with the gap, a read-out of the indicator corresponds to the discrete height of the expanded trial.

16. The expandable tibial tray trial of claim 15, wherein the head defines a transverse opening, which when aligned with the gap, indicates an initial starting position for the expandable trial.

17. A method for trialing an implant, the method comprising:

attaching a modular articular insert trial to an expandable trial;

positioning the expandable trial in a surgical site, the expandable trial having top and bottom plates, an actuation screw having a helical cut with step portions separated by a thread rise, and an expansion ramp having a pin configured to ride along the helical cut; and rotating the actuation screw to cause the expansion ramp to slide along the bottom plate and lift the top plate as the ramp translates forward, wherein when the pin rests in one step portion of the helical cut, the expandable trial is expanded to a discrete thickness.

18. The method of claim 17, wherein if the pin rests on the thread rise, the expandable trial cannot maintain its height under compression until one of the step portions is reached.

19. The method of claim 17, wherein when the step portion is reached during expansion, the pin falls into the step portion, thereby providing tactile feedback to a user.

20. The method of claim 17, wherein the actuation screw has one or more visual indicators to designate a given trial thickness, thereby providing visual feedback to a user.

* * * * *